United States Patent [19]
Bonutti

[11] Patent Number: 6,077,292
[45] Date of Patent: *Jun. 20, 2000

[54] METHOD AND APPARATUS FOR ANCHORING A SUTURE

[76] Inventor: Peter M. Bonutti, 1303 W. Evergreen Plz., Effingham, Ill. 62401

[*] Notice: This patent is subject to a terminal disclaimer.

[21] Appl. No.: 09/360,721

[22] Filed: Jul. 26, 1999

Related U.S. Application Data

[63] Continuation of application No. 08/929,168, Sep. 12, 1997, Pat. No. 5,941,900, which is a continuation of application No. 08/667,549, Jun. 21, 1996, Pat. No. 5,733,306, which is a division of application No. 08/452,310, May 26, 1995, Pat. No. 5,584,862, which is a division of application No. 08/291,970, Aug. 17, 1994, Pat. No. 5,549,630, which is a continuation-in-part of application No. 08/062,295, May 14, 1993, Pat. No. 5,403,348.

[51] Int. Cl.⁷ .................................................. A61B 17/04
[52] U.S. Cl. ........................................ 606/232; 606/139
[58] Field of Search ............................... 606/232, 72, 74, 606/139, 220, 144

[56] References Cited

U.S. PATENT DOCUMENTS

| | | |
|---|---|---|
| 4,409,974 | 10/1983 | Freedland . |
| 4,448,194 | 5/1984 | DiGiovanni et al. . |
| 4,669,473 | 6/1987 | Richards et al. ........................ 606/232 |
| 4,741,330 | 5/1988 | Hayhurst ................................. 606/232 |
| 4,750,492 | 6/1988 | Jacobs .................................... 606/232 |
| 4,823,794 | 4/1989 | Pierce ..................................... 606/232 |
| 4,898,156 | 2/1990 | Gatturna et al. ........................ 606/232 |
| 4,968,315 | 11/1990 | Gatturna ................................. 606/232 |
| 5,009,663 | 4/1991 | Broome . |
| 5,037,422 | 8/1991 | Hayhurst et al. ....................... 606/232 |
| 5,041,129 | 8/1991 | Hayhurst et al. ....................... 606/232 |
| 5,046,513 | 9/1991 | Gatturna et al. ........................ 606/232 |
| 5,053,047 | 10/1991 | Yoon ...................................... 606/232 |
| 5,100,417 | 3/1992 | Cercier et al. . |
| 5,102,421 | 4/1992 | Anspach, Jr. ........................... 606/232 |
| 5,123,914 | 6/1992 | Cope . |
| 5,141,520 | 8/1992 | Goble et al. ............................ 606/232 |
| 5,156,616 | 10/1992 | Meadows et al. . |
| 5,176,682 | 1/1993 | Chow . |
| 5,203,787 | 4/1993 | Noblitt et al. . |
| 5,324,308 | 6/1994 | Pierce . |
| 5,403,348 | 4/1995 | Bonutti .................................. 606/232 |
| 5,405,359 | 4/1995 | Pierce . |
| 5,522,846 | 6/1996 | Bonutti .................................. 606/232 |
| 5,540,718 | 7/1996 | Bartlett ................................... 606/232 |

FOREIGN PATENT DOCUMENTS 1903016 of 1970 Germany .

*Primary Examiner*—Gary Jackson
*Attorney, Agent, or Firm*—Tarolli, Sundheim, Covel, Tummino & Szabo LLP.

[57] ABSTRACT

A tubular anchor may have a polygonal cross-sectional configuration with flat outer side surfaces areas connected by a plurality of outer corner portions. A passage through the anchor may be formed by flat inner side surfaces interconnected by inner corner portions. A suture is inserted through the passage. A concentrated force may be applied against a limited area on a trailing end of the anchor to rotate the anchor to move an outer corner portion of the anchor into engagement with body tissue. The suture may engage an inner corner portion of the anchor. The suture may be inserted through a plurality of anchors and the anchors moved through a tubular member into the body tissue under the influence of force transmitted from a trailing anchor to a leading anchor. When the leading anchor is moved into the body tissue, it is rotated under the influence of force applied against a trailing end of the leading anchor. If desired, two anchors may be interconnected. A groove may advantageously be provided along the leading end and side of an anchor to receive the suture.

42 Claims, 10 Drawing Sheets

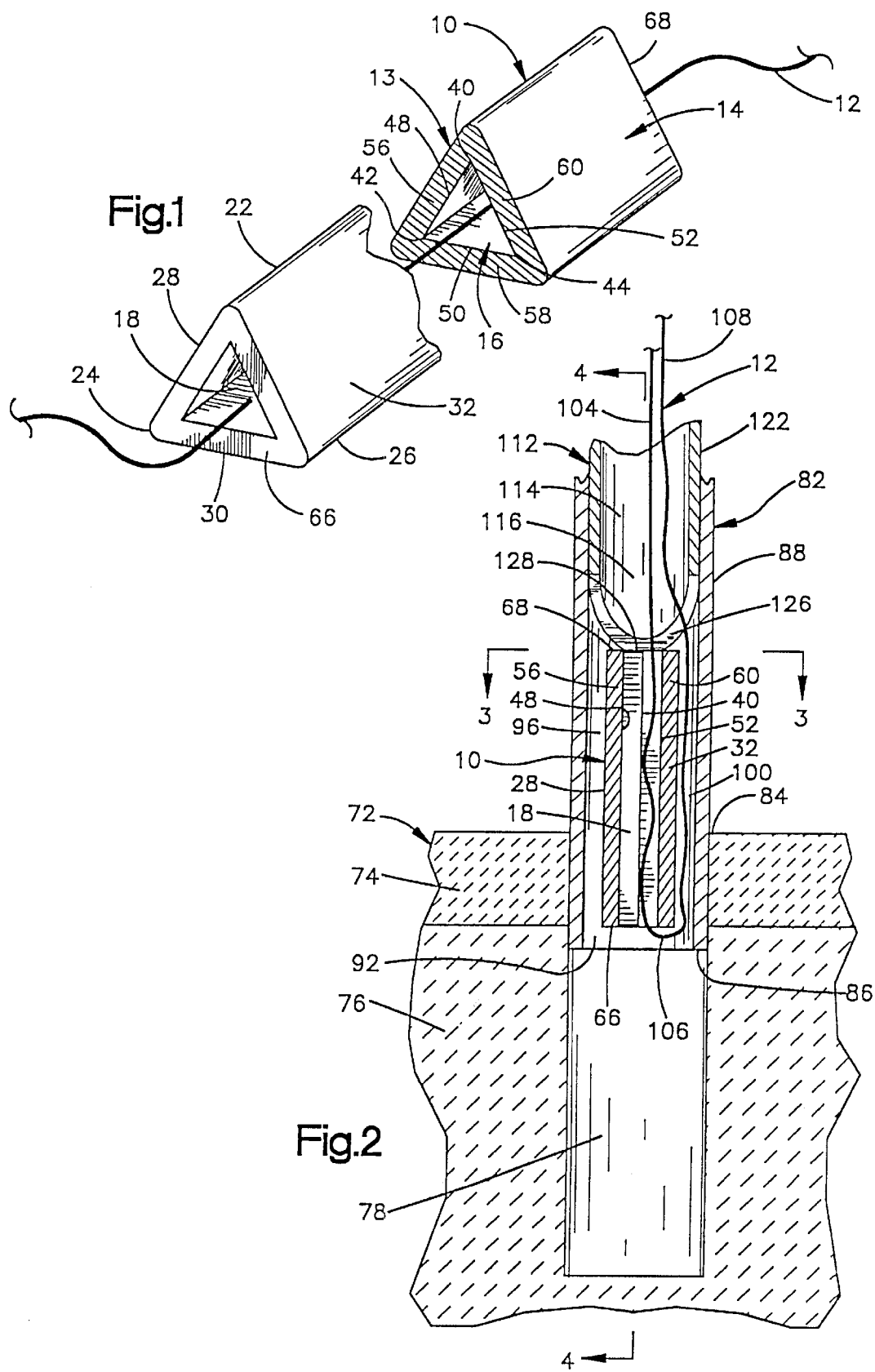

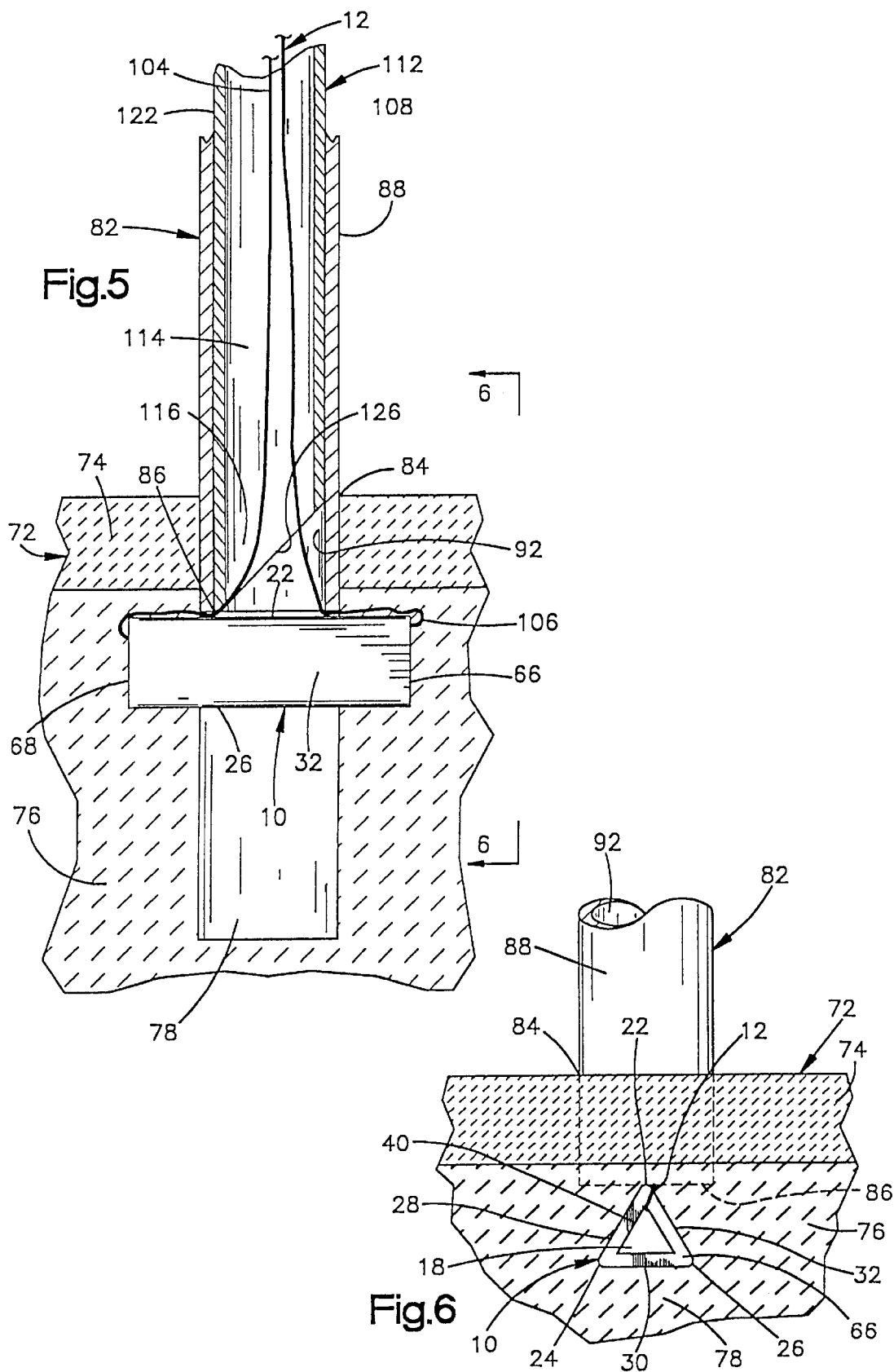

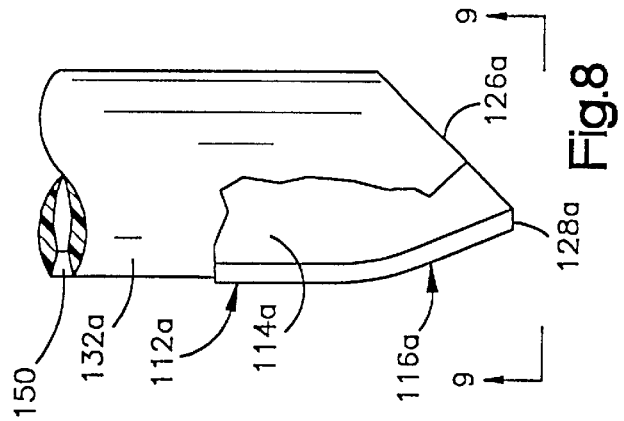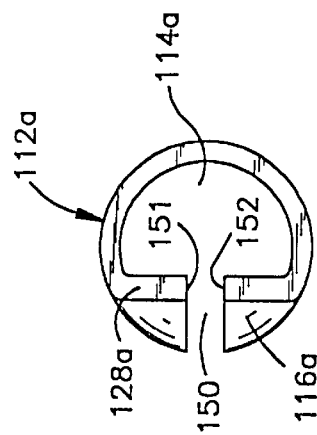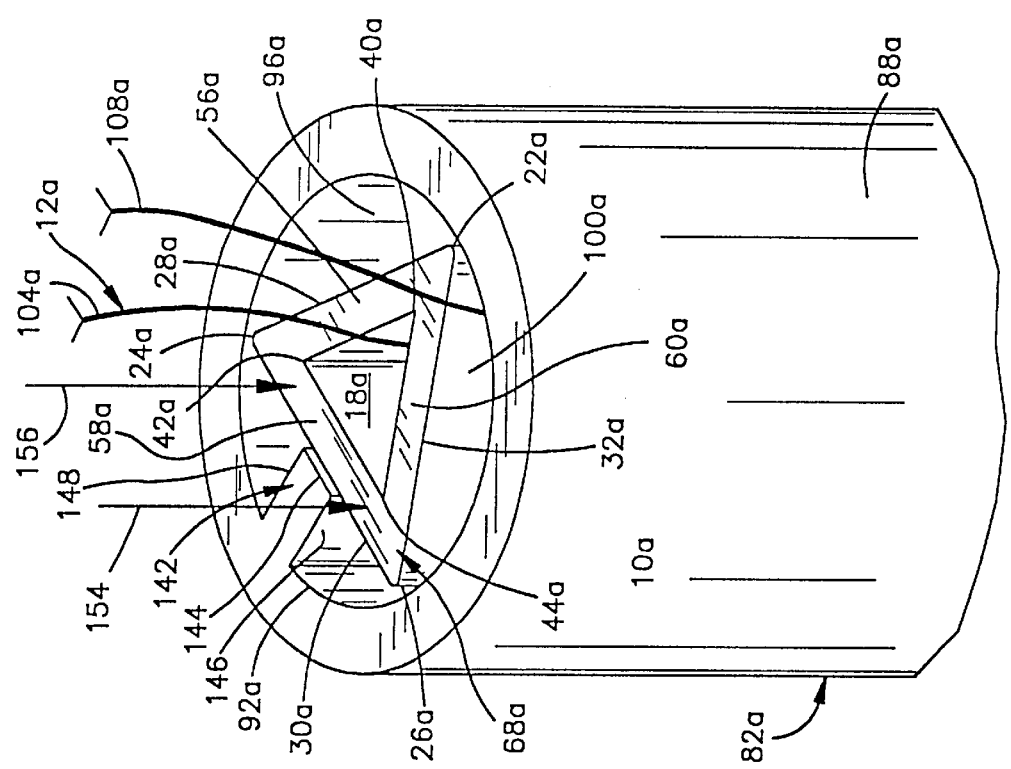

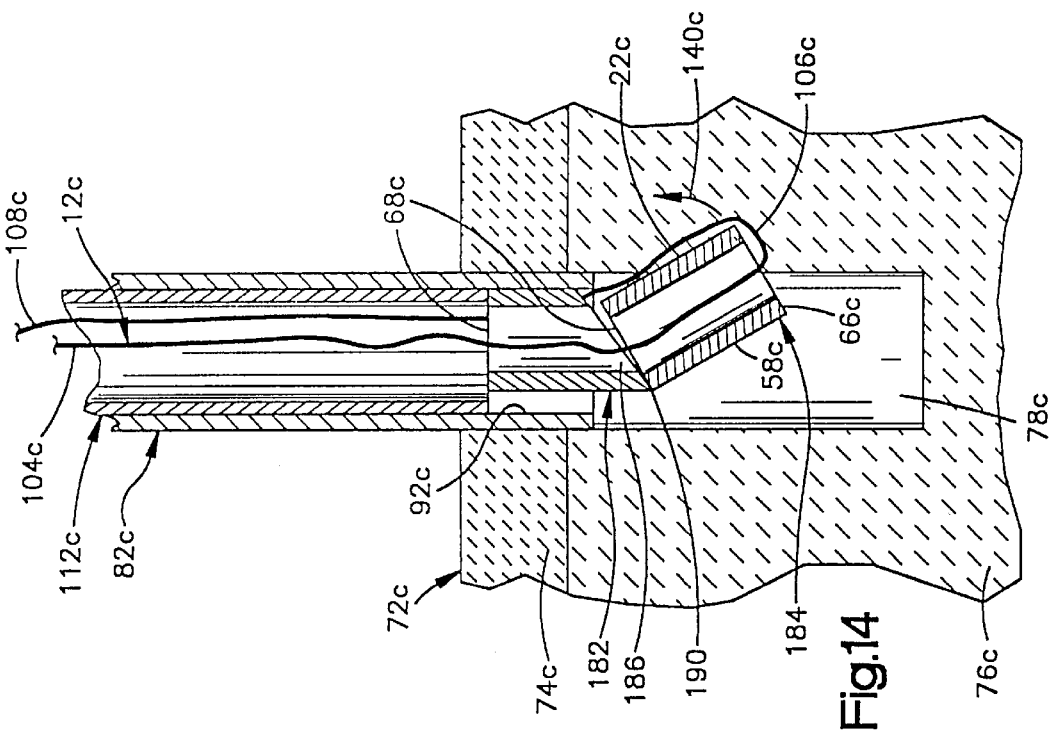
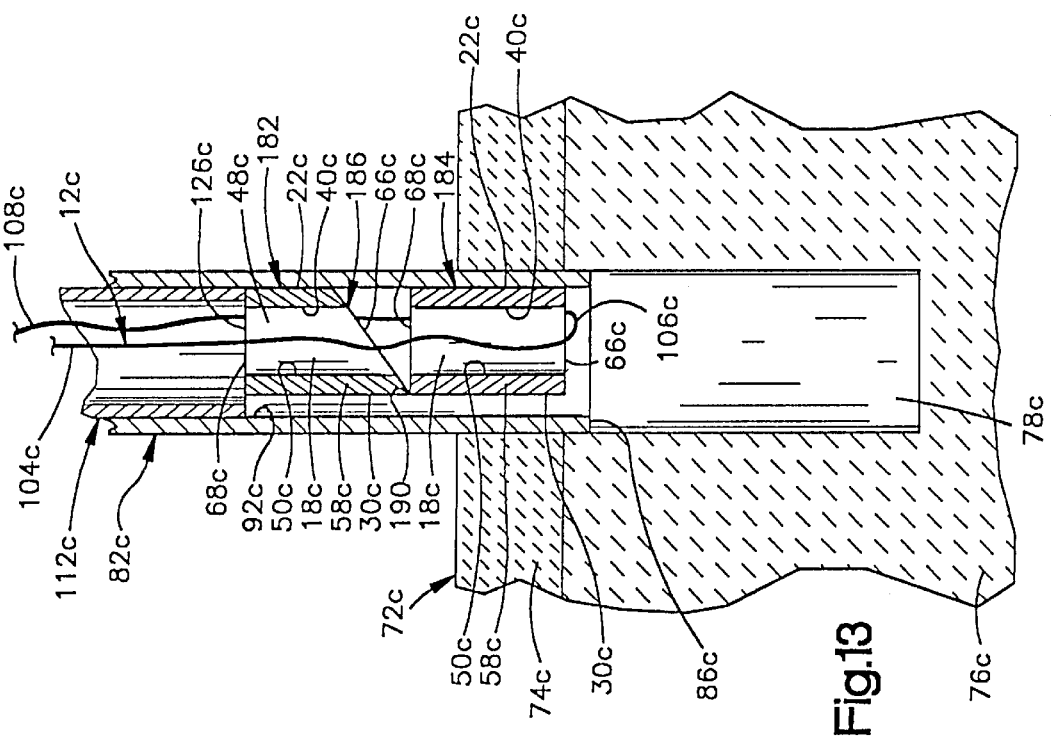

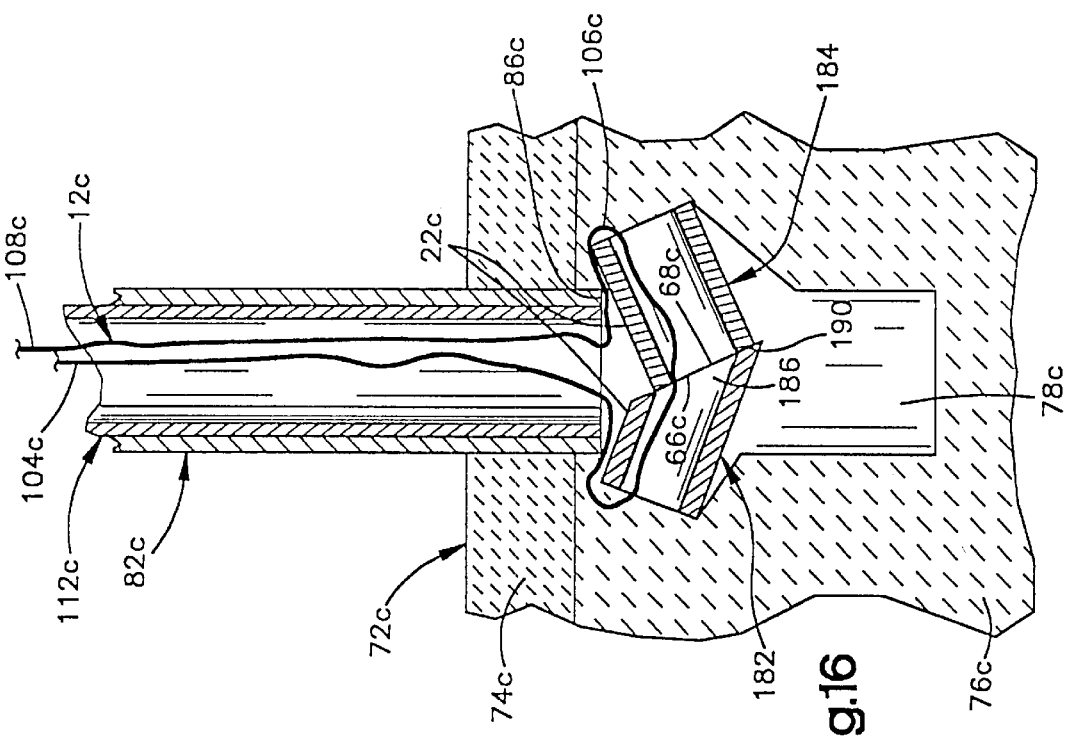
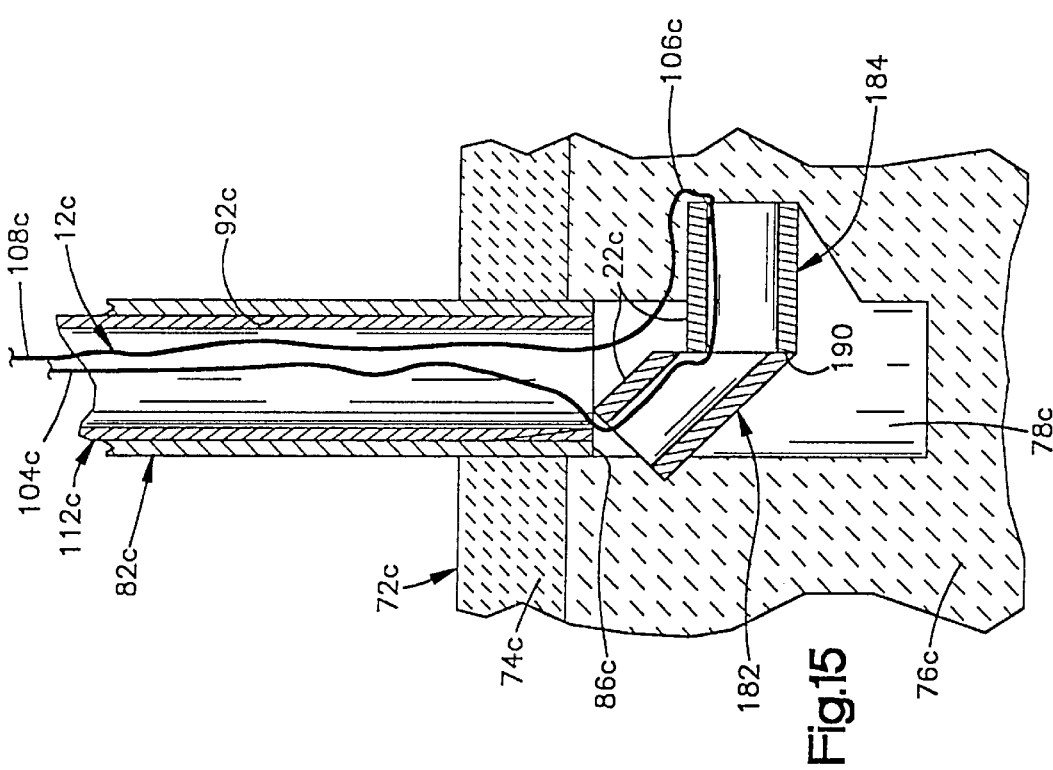

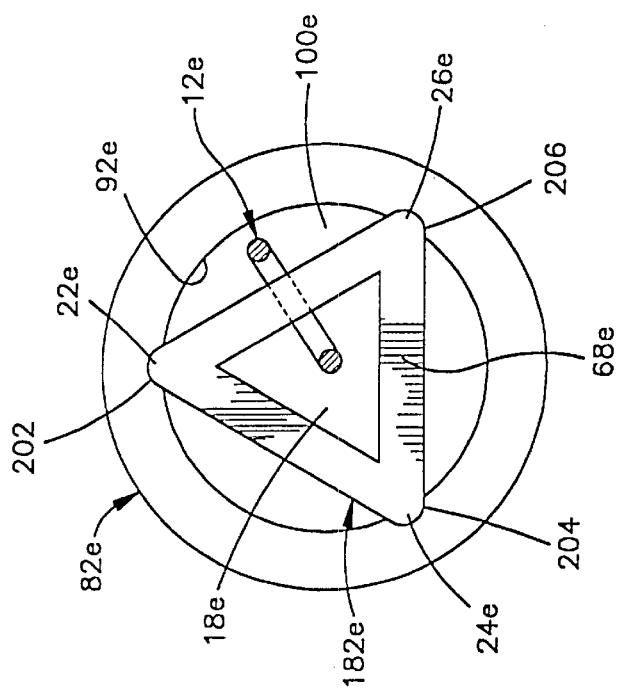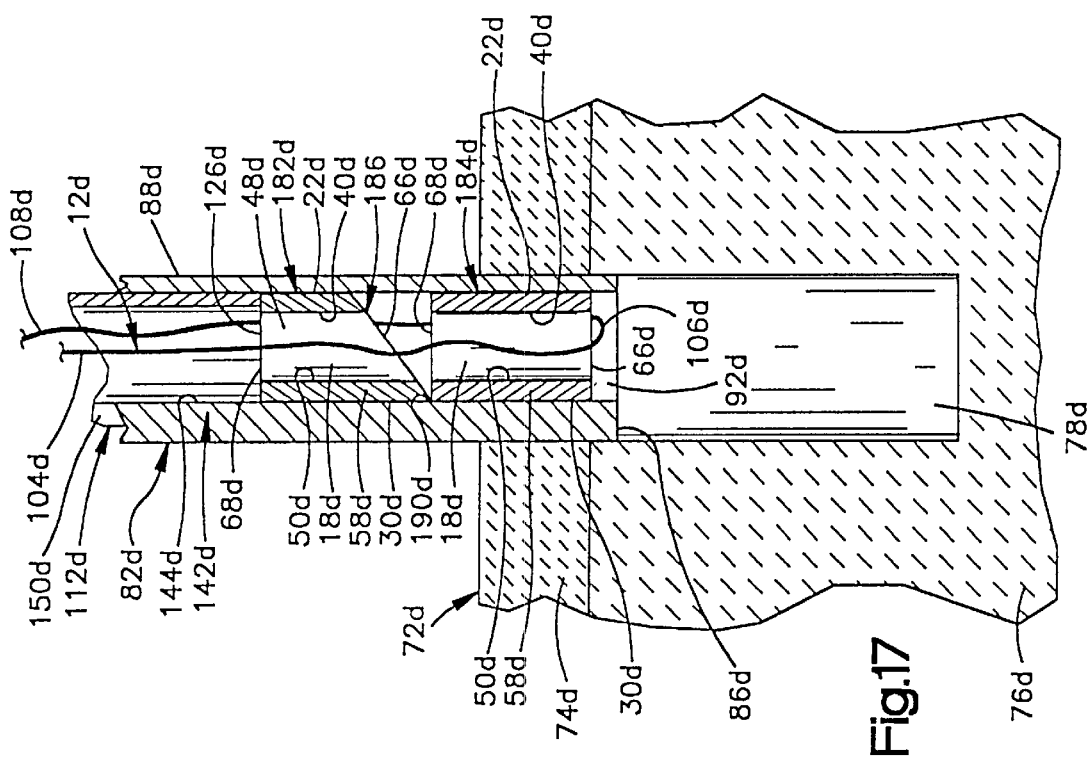

METHOD AND APPARATUS FOR ANCHORING A SUTURE

This application is a continuation of U.S. patent application Ser. No. 08/929,168, filed Sep. 12, 1997, now U.S. Pat. No. 5,941,900. The aforementioned application Ser. No. 08/929,168 is itself a continuation of U.S. patent application Ser. No. 08/667,549 filed Jun. 21, 1996, now U.S. Pat. No. 5,733,306. The aforementioned application Ser. No. 08/667,549 is itself a divisional of U.S. patent application Ser. No. 08/452,310 filed May 26, 1995 and issued as U.S. Pat. No. 5,584,862 on Dec. 17, 1996. The aforementioned application Ser. No. 08/453,310 is itself a divisional of U.S. patent application Ser. No. 08/291,970 filed Aug. 17, 1994 and issued as U.S. Pat. No. 5,549,630. The aforementioned application Ser. No. 08/291,970 is itself a continuation-in-part of U.S. patent application Ser. No. 08/062,295 filed May 14, 1993 and issued as U.S. Pat. No. 5,403,348. The benefit, under Title 35 United States Code, §120, of the aforementioned applications is hereby claimed.

BACKGROUND OF THE INVENTION

The present invention relates to a new and improved anchor and to a new and improved method of using one or more anchors to secure a suture in body tissue.

A known anchor and method of securing a suture in body tissue is disclosed in U.S. Pat. No. 5,041,129 issued Aug. 20, 1991. This patent discloses the use of a hollow outer needle or tube in which an anchor and pusher tube are received. A suture extends through the pusher tube and anchor. Force is applied against a trailing end of the anchor by the pusher tube to move the anchor through the hollow outer needle or tube into body tissue. Other known anchors for use in securing a suture in body tissue are disclosed in U.S. Pat. No. 5,176,682 issued Jan. 5, 1993, U.S. Pat. No. 4,968,315 issued Nov. 6, 1990 and U.S. Pat. No. 4,741,330 issued May 3, 1988.

SUMMARY OF THE INVENTION

An improved suture anchor has a polygonal cross-sectional configuration with an outer side which is formed by a plurality of flat side surface areas which are interconnected by outer corner portions. The anchor has a passage formed by a plurality of flat inner side surface areas which are interconnected by a plurality of inner corner portions. A suture is engageable with one of the inner corner portions to urge an outer corner portion of the anchor into engagement with body tissue. A groove may be provided in the end and/or outer side of the anchor to receive the suture.

A plurality of anchors having the configuration of the improved anchor described above or a different configuration may be used to anchor a suture. When a plurality of anchors are used, the suture is inserted through each of the anchors and the anchors are sequentially moved into the body tissue. As a leading anchor is moved into the body tissue, the suture is tensioned to move a corner portion on the leading anchor into engagement with the body tissue. A connector may be provided between each anchor.

BRIEF DESCRIPTION OF THE DRAWINGS

The foregoing and other features of the invention will become more apparent upon a consideration of the following description taken in connection with the accompanying drawings, wherein:

FIG. 1 is a fragmentary pictorial illustration depicting the relationship between an anchor constructed in accordance with one of the features of the present invention and a suture;

FIG. 2 is a fragmentary sectional view, illustrating a method in accordance with another feature of the invention and by which the anchor of FIG. 1 is moved into body tissue;

FIG. 5 is a fragmentary sectional view, generally similar to FIG. 4, illustrating the manner in which the suture is tensioned to urge a corner portion of the anchor into engagement with body tissue;

FIG. 6 is a fragmentary sectional view taken generally along the line 6—6 of FIG. 5, further illustrating the relationship between the corner portion of the anchor, the body tissue and the tubular guide member;

FIG. 7 is a schematicized fragmentary pictorial view illustrating the relationship of the anchor of FIG. 1 to an embodiment of the tubular guide member having a locating surface which positions the anchor in a desired orientation relative to the tubular guide member;

FIG. 8 is a fragmentary cross-sectional view illustrating the construction of a pusher member used with the tubular guide member of FIG. 7;

FIG. 9 is an end view, taken generally along the line 9—9 of FIG. 8, further illustrating the construction of the pusher member;

FIG. 13 is a fragmentary sectional view, generally similar to FIG. 2, illustrating the manner in which a suture extends through a plurality of anchors and the plurality of anchors are moved through a tubular member into body tissue;

FIG. 14 is a fragmentary sectional view, generally similar to FIG. 13, illustrating the manner in which a leading anchor of the plurality of anchors is rotated relative to a trailing anchor as the leading anchor moves out of the tubular member;

FIG. 15 is a fragmentary sectional view, generally similar to FIG. 14, illustrating the manner in which the trailing anchor moves out of the tubular member;

FIG. 16 is a fragmentary sectional view, generally similar to FIG. 15, illustrating the manner in which the leading and trailing anchors are urged into engagement with body tissue by tensioning of the suture;

FIG. 17 is a fragmentary sectional view, generally similar to FIG. 13, illustrating the manner in which a plurality of anchors cooperate with a tubular guide member having the same construction as the tubular guide member of FIG. 7;

FIG. 18 is an enlarged sectional view, generally similar to FIG. 3, illustrating the manner in which an anchor engages longitudinally extending grooves inside a tubular guide member;

DESCRIPTION OF SPECIFIC PREFERRED EMBODIMENTS OF THE INVENTION

Anchor

Figure 3:
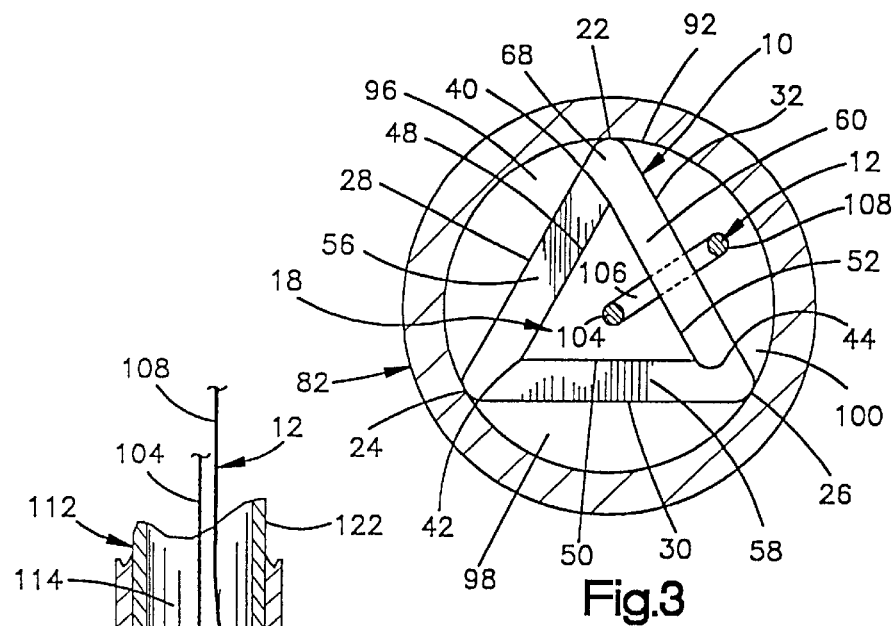
FIG. 3 is an enlarged sectional view, taken generally along the line 3—3 of FIG. 2, illustrating the relationship of the anchor to a tubular guide member and to a suture.

An anchor 10 (FIG. 1) constructed in accordance with one of the features of the present invention may be used to secure a suture 12 in hard or soft body tissue. The anchor 10 has a tubular wall 13 with an outer side 14 and an inner side 16. The inner side 16 defines a passage 18 which extends through the anchor 10.

The outer side 14 of the tubular wall 13 has a polygonal cross-sectional configuration. Thus, the outer side 14 of the anchor 10 includes a plurality of longitudinally extending outer corner portions 22, 24, and 26. The outer corner portions 22, 24 and 26 are linear and interconnect a plurality of flat rectangular outer side surface areas 28, 30, and 32.

In the specific preferred embodiment of the anchor 10 illustrated in FIG. 1, the tubular wall 13 has an equilateral triangular cross-sectional configuration and forms a hollow prism. Therefore, the angles between the outer side surface areas 28, 30 and 32 at each of the corner portions 22, 24 and 26 is the same, that is, an angle of 120°. It should be understood that the outer side 14 of the anchor 10 could have a different configuration if desired.

For example, the outer side 14 of the anchor 10 could have a cross-sectional configuration corresponding to the configuration of a segment of a circle. An anchor 10 with an outside surface with such a configuration would have a pair of flat rectangular outer side surface areas. These surface areas would be interconnected by a corner portion. An arcuate surface area would extend between the flat outer side surface areas at a location opposite from the corner portion.

The inner side 16 of the anchor 10 has a polygonal cross-sectional configuration which corresponds to and is aligned with the polygonal outer side 14 of the anchor. The inner side 16 of the anchor 10 defines open ends of the passage 18 which extends through the anchor. Thus, the inner side 16 of the anchor has longitudinally extending inner corner portions 40, 42, and 44. The inner corner portions 40, 42 and 44 are linear and are aligned with and extend parallel to the outer corner portions 22, 24, and 26 and to a longitudinal central axis of the anchor 10.

In addition, the inner side 16 of the anchor 10 includes flat rectangular inner side surface areas 48, 50, and 52 which are interconnected by the inner corner portions 40, 42 and 44. The inner side surface areas 48, 50 and 52 extend parallel to and are spaced equal distances from the outer side surface areas 28, 30 and 32. The inner side 16 has a triangular cross-sectional configuration and is aligned with the outer side 14. Thus, the inner side 16 has a longitudinal central axis which is coincident with a longitudinal central axis of the outer side 14.

It is contemplated that the inner side 16 and outer side 14 could have different configurations. For example, the inner side 16 could be formed with a cross-sectional configuration which corresponds to the configuration of a circle or a segment of a circle. If desired, the inner side 16 could be formed as an almost complete cylinder with a radially extending corner portion which has a circumferential extent of, for example, 40° of the inner side.

In the embodiment of the anchor 10 illustrated in FIG. 1, the tubular wall 13 has three side walls 56, 58 and 60 which are of the same size. The side walls 56, 58 and 60 form rectangular sections of the tubular wall 13. However, it should be understood that the side walls 56, 58 and 60 could have a different configuration and that a greater or lesser number of side walls could be provided if desired.

In one specific embodiment of the anchor 10, the anchor had the configuration illustrated in FIG. 1 and was formed of stainless steel to ASTM designation F-138-86 specification. This specific embodiment of the anchor 10 had a length of 3.10 millimeters. Each of the rectangular side walls 56, 58 and 60 had a width of 1.83 millimeters. The side walls 56, 58 and 60 had a thickness of 0.5 millimeters. The outer corner portions 22, 24 and 26 had a radius of 0.3 millimeters and the inner corner portions 40, 42 and 44 had a radius of 0.15 millimeters.

In another specific embodiment of the invention, the anchor 10 was also formed of stainless steel having an ASTM designation F-138-86 specification. This embodiment of the anchor had a length of 7.2 millimeters. Each of the rectangular side walls 56, 58 and 60 had a width of 1.83 millimeters. The side walls had a thickness of 0.5 millimeters. Both of the specific foregoing examples of the anchor 10 had the hollow prism-shaped configuration illustrated in FIG. 1.

It should be understood that the foregoing specific dimensions and materials for specific examples of the anchor 10 have been set forth herein for purposes of clarity of description. It is contemplated that the anchor 10 could be made with dimensions which are different than the specific dimensions set forth above. However, it is believed that it may be advantageous to make the anchor 10 with a length of from 2 to 8 millimeters and a width of 1.0 to 2.5 millimeters. Of course, the specific dimensions of the anchor 10 can be varied depending upon the environment in which the anchor is to be utilized to secure a suture 12.

In accordance with another of the features of the invention, the anchor 10 is installed in body tissue in an orientation in which one of the outer corner portions 22, 24 or 26 is embedded in body tissue by force applied against an adjacent inner corner portion 40, 42 or 44 by the suture 12. Force applied by the suture 12 against one of the inner corner portions 22, 24 or 26 of the anchor 10 presses the flat outer side surface areas which are interconnected by the embedded corner portion against the body tissue. Thus, if the suture 12 applies force against the inner corner portion 40, the outer corner portion 22 becomes embedded in the body tissue and the flat outer side surface areas 28 and 32 are pressed against the body tissue.

The outer corner portions which are spaced from the embedded outer corner portion 22, 24 or 26 cooperate with the body tissue to stabilize the anchor 10 and hold it against sidewise movement. Parallel flat end surfaces 66 and 68 on the anchor 10 extend perpendicular to the outer side surfaces 28, 30 and 32 and cooperate with the body tissue to retain the anchor against axial movement relative to the body tissue. The cooperation between the outer corner portions 22, 24 and 26 and outer side surfaces 28, 30 and 32 with the body tissue securely retains the anchor 10 in place in the body tissue.

Installation Apparatus

When the anchor 10 is to be installed in human body tissue, the anchor may be pushed directly into the body tissue or into a recess may be formed in the body tissue to receive the anchor. The anchor 10 may be installed in either hard or soft body tissue. In FIGS. 2, 4, 5 and 6, the anchor 10 is to be installed in bone 72 in a human body. The bone 72 includes a compact outer layer 74 and a more porous cancellous tissue 76 which is surrounded by the compact outer layer.

A cylindrical recess or cavity 78 may be formed in the bone tissue to receive the anchor 10 in the manner illustrated in FIG. 2. It should be understood that the anchor 10 may be used with soft tissue rather than the hard tissue of the bone 72. It should also be understood that, if desired, the formation of the recess or cavity 78 may be omitted.

A tubular guide member 82 (FIGS. 2–6) is inserted into the recess 78 (FIG. 2). Although the tubular guide member 82 could have many different configurations, the illustrated guide member 82 is cylindrical and is inserted through a circular opening 84 to the recess 78. The guide member 82 is inserted through the compact outer layer 74 of bone tissue. A circular open inner end 86 of the guide member 82 is disposed immediately below (as viewed in FIG. 2) the inner side of the compact outer layer 74 of bone tissue 72.

The tubular guide member 82 has a cylindrical outer side surface 88 with a diameter which is substantially the same as the diameter of the cylindrical recess 78 and the circular opening 84 to the recess. Therefore, the bone tissue 82 firmly engages the outer side surface 88 of the guide member 72 to hold the guide member in position relative to the recess 78. The recess 78 extends inward past the lower (as viewed in FIG. 2) end 86 of the guide member 82 for a distance which is at least as great as the length of the anchor 10, that is at least as great as the distance from the end surface 66 to the end surface 68 (FIG. 1) of the anchor 10.

The tubular guide member 82 has a cylindrical inner side surface 92 (FIG. 3). When the anchor 10 is to be installed in the bone tissue 72, the anchor is positioned in the guide member 82 with the end surface 66 on the anchor leading (FIG. 2) and the end surface 68 on the anchor 10 trailing. The outer corner portions 22, 24 and 26 of the anchor 10 are disposed in engagement with the inner side surface 92 (FIG. 3) of the guide member 82 at equally spaced increments (approximately 120°) about the inner side surface of the guide member. A longitudinal central axis of the anchor 10 is coincident with a longitudinal central axis of the guide member 82.

The outer side surface areas 28, 30 and 32 (FIG. 3) of the anchor 10 are spaced from the inner side surface 92 of the guide member 82. The outer side surface areas 28, 30 and 32 extend parallel to a longitudinal central axis of the guide member 82. The outer side surface areas 28, 30 and 32 on the anchor 10 cooperate with the inner side surface area 92 on the guide member 82 to form a plurality, of channels 96, 98 and 100 between the anchor 10 and the inner side surface 92 of the guide member 82. The channels 96, 98 and 100 extend axially along the length of the anchor 10.

A portion 104 (FIG. 2) of the suture 12 extends downward (as viewed in FIG. 2) through the upper portion of the guide member 82 into the passage 18 in the anchor 10. A relatively short portion 106 of the suture 12 extends across the leading end surface 66 of the anchor 10. A second relatively long portion 108 of the suture 12 extends upward along the outer side surface area 32 of the anchor 10 through the channel 100. The relatively long portions 104 and 108 of the suture 12 extend from the guide member 82 to a location offset to one side of the recess 78 in the bone tissue 72.

Once the anchor 10 has been inserted into the tubular guide member 82 in the manner shown in FIGS. 2 and 3, a hollow cylindrical pusher member 112 (FIG. 2) is inserted into the guide member 82 through an open upper or outer end of the guide member. The pusher member 112 extends through the open upper or outer end of the guide member 82. The distance to which the pusher member 112 extends into telescopic engagement with the guide member 82 can be varied by moving the pusher member axially relative to the guide member. Although the pusher member 112 could have a configuration which is different than the cylindrical configuration of the guide member 82, it is preferred to utilize a pusher member having the same configuration as the guide member.

The suture 12 extends through a cylindrical passage 114 formed in the tubular pusher member 112. Thus, the portion 104 of the suture 12 extends into the pusher member 112 from a location offset to one side of the recess 78 in the bone tissue 72. The portion 104 of the suture 12 extends through the passage 114 in the pusher member 112 to the passage 18 in the anchor 10. The portion 106 of the suture 12 extends across the leading end 66 of the anchor 10.

The portion 108 of the suture 12 extends upward through the channel 100 along the outer side of the anchor 10 (FIGS. 2 and 3). The portion 108 of the suture 12 then extends through an open lower or inner end portion 116 (FIG. 2) of the pusher member 112 into the passage 114 in the tubular pusher member. The portion 108 of the suture 12 then extends from the open upper end of the pusher member to a location which is offset to one side of the recess 78. A surgeon can manually grip the suture 12 adjacent to an open upper end of the pusher member 112.

The pusher member 112 has a cylindrical outer side surface 122 which telescopically engages the cylindrical inner side surface 92 of the guide member 82. The cylindrical outer side surface 122 of the pusher member 112 has a diameter which is just slightly less than the diameter of the cylindrical inner side surface 92 of the guide member 82. Therefore, the pusher member 112 can slide freely along the inner side surface 92 of the guide member 82 while the guide member holds the inner side surface of the cylindrical pusher member in alignment with the longitudinal central axis of the anchor 10 (FIG. 2). Thus, the cylindrical inner side surface 92 of the guide member 82 engages the outer corner portions 22, 24 and 26 of the anchor 10 to guide movement of the anchor and engages the outer cylindrical side surface 122 of the pusher member 112 to guide movement of the pusher member.

Figure 4:
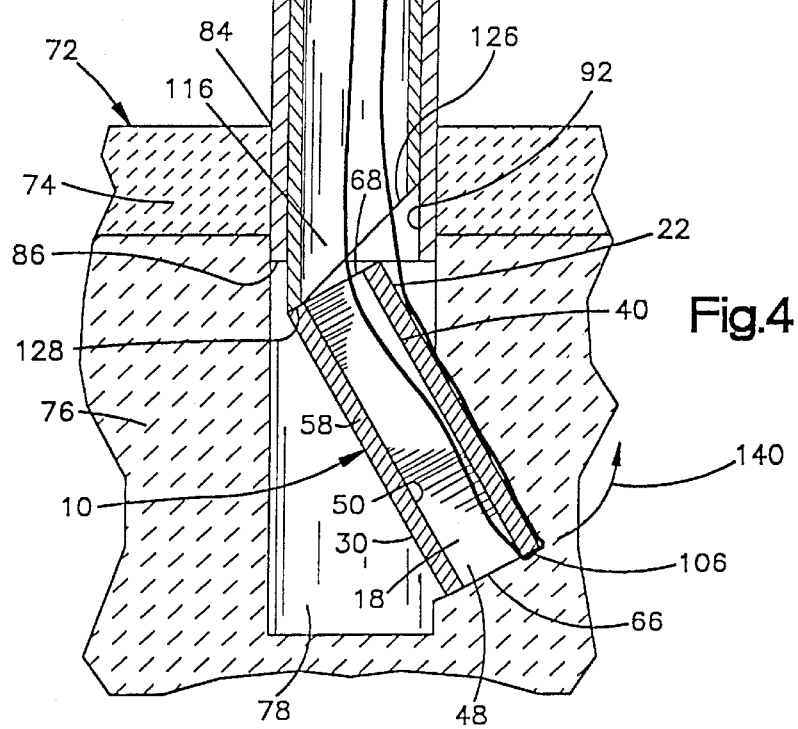
FIG. 4 is a fragmentary sectional view, taken along the line 4—4 of FIG. 2, illustrating the manner in which force is concentrated against a trailing end portion of the anchor by a pusher member to promote rotational movement of the anchor relative to body tissue.

The open end portion 116 of the pusher member 112 is axially tapered to enable the pusher member 112 to apply a concentrated force against the trailing end surface 68 (FIG. 2) of the anchor 10. Thus, the pusher member 112 has a lower (as viewed in FIG. 2) end surface 126 which is skewed at an acute angle to a longitudinal central axis of the pusher member (FIG. 4). In addition, the pusher member 112 has a flat end surface 128 which engages the trailing end surface 68 of the anchor 10.

The flat end surface 128 has a length and width which enables it to engage the trailing end surface 68 of the anchor regardless of the orientation of the pusher member 112 relative to the trailing end surface 68 of the anchor. This enables the pusher member 112 to engage the trailing end surface 68 of the anchor at a location adjacent to one of the outer corner portions 22, 24 or 26 (FIG. 2) of the anchor and/or to engage the anchor at a location adjacent to one of the outer side surface areas 28, 30 or 32 of the anchor.

The tapered configuration of the open end portion 116 of the pusher member 112 results in the pusher member applying a concentrated force against the trailing end surface 68 of the anchor at a location which is offset from the central axis of the anchor. Since the force applied by the pusher member 112 to the trailing end surface 68 of the anchor is offset from the central axis of the anchor 10, a torque is applied to the anchor which tends to rotate the anchor about an axis extending through the location where the end portion 116 of the pusher member 112 engages the trailing end surface 68 of the anchor.

When the anchor 10 is in the guide member 82 (FIGS. 2 and 3), the outer corner portions 22, 24 and 26 of the anchor member engage the cylindrical inner side surface 92 of the guide member 82 to retain the anchor against rotational movement under the influence of the concentrated force applied against the trailing end surface 68 of the anchor by the pusher member 112. Thus, the cylindrical inner side surface 92 of the guide member 82 cooperates with the anchor 10 to retain the longitudinal central axis of the anchor 10 coincident with the longitudinal central axis of the guide member. In addition, the cylindrical inner side surface 92 of the guide member 82 cooperates with a cylindrical outer side surface 132 of the pusher member 112 to retain the pusher member in an orientation in which the longitudinal central axis of the pusher member is coincident with the longitudinal central axis of the guide member 82.

In the embodiment of the invention illustrated in FIGS. 2 and 3, the guide member 82 and the pusher member 112 both have cylindrical configurations. However, it is contemplated that the pusher member 112 and guide member 82 could have different configurations. For example, the guide member 82 and the pusher member 112 could both have triangular cross-sectional configurations. If desired, the guide member 82 could have a circular cross-sectional configuration and the pusher member 112 could have a triangular cross-sectional configuration.

Installation Procedures

When the anchor 10 is to be installed in body tissue, which may be either hard or soft tissue, the suture 12 is inserted through the passage 18 (FIG. 2) in the anchor 10. The relatively long portion 104 of the suture 12 extends through the passage 18 to the portion 106 of the suture. The portion 106 of the suture extends across the end surface 66 of the anchor. The portion 108 of the suture extends along the outer side 13 of the anchor 10. In FIG. 2, the portion 108 of the suture 12 extends along the outer side surface area 32. However, the portion 108 of the suture 12 could extend along any one of the outer side surface areas 28, 30 or 32.

Once the suture 12 has been inserted through the passage 18 in the anchor 10, the anchor is inserted into the guide member 82. As this is done, the outer corner portions 22, 24 and 26 (FIG. 3) of the anchor engage the inner side surface 92 of the guide member 82 to position the anchor relative to the guide member. The portion 108 of the suture 12 extends through the channel 100 formed between the outer side surface area 32 on the anchor 10 and the inner side surface 92 of the guide member 82. The guide member 82 retains the anchor 10 in an orientation in which a longitudinal central axis of the anchor is coincident with a longitudinal central axis of the guide member.

Either before or after the anchor 10 is inserted into the guide member 82, the suture 12 is inserted through the open ended passage 114 (FIG. 2) in the pusher member 112. After the anchor 10 has been inserted into the guide member 82, the pusher member 112 is inserted into the guide member. The open leading end portion 116 of the pusher member 112 is moved into engagement with the trailing end surface 68 of the anchor 10.

The pusher member 112 is pressed against the trailing end surface 68 of the anchor 10 to move the anchor through the guide member 82 toward the recess 78 in the bone 72. As this is occurring, the anchor 10 and pusher member 112 may rotate relative to each other and to the guide member 82 about their coincident central axes. However, the inner side surface 92 of the guide member 82 engages the corner portions 22, 24, and 26 of the anchor 10 to retain the anchor against rotational movement about an axis extending transversely to and offset from the longitudinal central axis of the anchor. Thus, the corner portions 22, 24 and 26 on the anchor 10 slide along the inner side surface 92 of the guide member 82 to maintain the longitudinal central axis of the anchor coincident with the longitudinal central axis of the guide member.

A concentrated force is applied against the trailing end surface 68 of the anchor by the tapered end portion 116 of the pusher member 112. The pusher member 112 applies the concentrated force against the anchor 10 at a location which is offset to one side of the longitudinal central axis of the anchor 10. Thus, the flat end surface 128 on the tapered end portion 116 of the pusher member 112 engages the anchor 10 at a trailing end of one of the corner portions 22, 24 or 26 and/or a trailing end of one of the sidewalls 56, 58 or 60. The tapered end portion 116 of the pusher member 112 has a radial thickness which is sufficient to enable the tapered end portion to span one of the channels 96, 98 or 100 (FIG. 3) to engage the trailing end of a sidewall 56, 58 or 60 at a location spaced from the corner portions 22, 24 and 26 of the anchor 10.

Engagement of the tapered end portion 116 of the pusher member 112 with the trailing end of the anchor 10 at a location offset to one side of the longitudinal central axis of the anchor results in the application of torque to the anchor. This torque tends to rotate the anchor about an axis extending through the location where the tapered end portion 116 of the pusher member 112 engages the trailing end surface 68 on the anchor. The outer corner portions 22, 24 and 26 of the anchor 10 engage the inner side surface 92 of the guide member 82 to hold the anchor against rotation under the influence of the torque applied to the anchor by the pusher member 112 as the anchor moves through the guide member.

As the pusher member 112 moves downward (as viewed in FIG. 2) relative to the guide member 82, the anchor 10 is pushed downward in the guide member. As this occurs the anchor 10 pulls the suture downward. Thus, force is transmitted from the leading end surface 66 of the anchor 10 to the portion 106 of the suture 12 to pull the suture into the pusher member 112 and guide member 82.

As the anchor continues to move downward (as viewed in FIG. 2), the leading end of the anchor and the portion 106 of the suture 12 emerge from the open lower end 86 of the guide member 82 into the recess 78. As the anchor 10 moves through the open lower (as viewed in FIG. 2) end portion of the guide member 82, the suture 12 is tensioned to apply force against the leading end surface 66 of the anchor. The surgeon pulls on the portions 104 and 108 of the suture 12 to tension the suture. This force pulls the anchor upward (as viewed in FIG. 2) against the pusher member 112.

As the suture is tensioned and the trailing end portion of the anchor 10 begins to move out of the guide member 82, the suture slides along one of the inner side surface areas 48, 50 or 52 on the anchor into one of the inner corner portions 40, 42 or 44. This tends to rotate the anchor about its longitudinal central axis relative to the pusher member 112 to move one of the side walls 56, 58 or 60 on the anchor into alignment with the tapered end portion 116 of the pusher member 112. As this occurs, the force applied by the tapered end portion 116 of the pusher member 112 becomes concentrated at the trailing end portion of one of the side walls 56, 58 or 60 of the anchor.

For example, the anchor 10 rotates about its central axis from the position shown in FIG. 2 to the position shown in FIG. 4. When this occurs, the surface 126 on the tapered leading end portion 116 of the pusher member 112 engages the trailing end of the side wall 58 (FIG. 1) of the anchor 10.

This results in the force applied by the pusher member 112 being concentrated at a location which is opposite from the outer corner portion 22 of the anchor. By concentrating the force applied against the trailing end surface 68 of the anchor by the pusher member 112 at a location opposite from the corner portion 22, the torque applied to the anchor 10 by the pusher member 112 tends to rotate the anchor in a clockwise direction, as indicated by the arrow 140 in FIG. 4.

Simultaneously with rotation of the anchor 10 about its central axis, the tension in the suture 12 applies force against the leading end surface 66 of the anchor. The force applied against the leading end 66 of the anchor 10 by the suture 12 pulls the trailing end 68 of the anchor back or upward (as viewed in FIG. 4) toward the tapered leading end portion 116 of the pusher member 112. Therefore, the tension in the suture 12 tends to further rotate the anchor 10 in a counterclockwise direction (as viewed in FIG. 4), in the manner indicated schematically by the arrow 140. The inner corner portion 40 of the anchor 10 holds the suture 12 against sidewise movement relative to the anchor and concentrates the force applied by the suture to the anchor at the inner corner portion of the anchor.

Under the combined influence of the concentrated force applied against the trailing end surface 68 of the anchor 10 by the pusher member 112 and the force applied against the inner corner portion 40 of the anchor adjacent to the leading end surface 66 by the suture 12, the anchor is rotated into the cancellous bone tissue 76, in the manner indicated schematically by the arrow 140 in FIG. 4. Thus, the anchor 10 is rotated about an axis which extends perpendicular to and is offset from the central axis of the guide member 82. The axis about which the anchor 10 rotates extends through the location where the leading end surface 128 on the pusher member 112 engages the trailing end surface 68 on the anchor 10. As this occurs, the pusher member 112 continues to move axially downward (as viewed in FIG. 4) in the guide member 82 into the recess 78. The anchor 10 continues to rotate about the axis extending through the location where the end surface 128 on the pusher member 112 engages the end surface 68 on the anchor 10 until the surface 68 on the anchor moves into abutting engagement with the sloping end surface 126 on the pusher member 112.

The combination of concentrated force pushing against the trailing end surface 68 of the anchor on one side of the longitudinal central axis of the anchor and a pulling force applied against the leading end surface 66 at a corner portion of the anchor on the opposite side of the longitudinal central axis of the anchor results in a substantial counterclockwise (as viewed in FIG. 4) torque which causes the anchor to rotate against the resistance provided by the soft cancellous tissue 76 of the bone 72. This results in the anchor 10 moving from the upright orientation shown in FIG. 2 through the orientation shown in FIG. 4 toward an orientation in which the trailing end surface 68 on the anchor 10 engages the sloping end surface 126 on the pusher member 112.

When the trailing end surface 68 on the anchor 10 engages the sloping end surface 126 (FIG. 4) on the pusher member 112, the central axis of the anchor extends perpendicular to the sloping end surface 126 and is skewed at an angle of 45° to the central axis of the guide member 82. The pusher member 112 is then withdrawn into the guide member 82. As the pusher member 112 is moved axially upward as viewed in FIG. 4 into the guide member 82, the force applied by the suture 12 against the leading end 66 of the anchor 10 continues in counterclockwise rotation of the anchor. The force applied against the leading end portion 66 of the anchor by the suture 12 presses the trailing end portion 68 of the anchor against the left (as viewed in FIGS. 4 and 5) side surface of the recess 78.

Continued pulling or tensioning of the suture 12 results in the outer corner portion 22 of the anchor 10 being pulled upward toward the inner or lower (as viewed in FIG. 5) end surface 86 of the guide member 82. As this occurs, the force transmitted from the suture 12 to the anchor 10 pulls the trailing end of the anchor toward the left, as viewed in FIG. 4. Thus, the anchor 10 is first moved toward the right (as viewed in FIG. 4) of the central axis of guide member 82 under the combined influence of force applied against the anchor by the pusher member 112 and the suture 12. The pusher member 112 is then slowly withdrawn and, simultaneously therewith, the anchor 10 is moved toward the right (as viewed in FIGS. 4 and 5) under the influence of force applied against the anchor by tension in the suture 12. The suture 12 is tensioned by the surgeon when he or she manually pulls on the suture.

The force on the anchor 10 causes it to move to the substantially horizontal orientation shown in FIGS. 5 and 6. At this time, the longitudinal central axis of the anchor 10 and the outer corner portions 22, 24 and 26 of the anchor extend perpendicular to the coincident longitudinal central axes of the guide member 82 and pusher member 112. The tension force in the suture 12 pulls the outer corner portion 22 of the anchor 10 upward toward the lower end of the guide member 82.

As this is occurring, the outer corner portion 22 of the anchor 10 becomes embedded in the relatively soft cancellous bone tissue 76 (FIG. 6). In addition, the flat outer side surface areas 28 and 32 press against the cancellous bone tissue to stabilize the anchor 10. The outer corner portions 24 and 26 opposite from the corner portion 22, cooperate with the cancellous bone tissue 76 to further stabilize the anchor and retain the anchor 10 against movement relative to the body tissue 72.

The polygonal configuration of the anchor 10 results in the anchor being retained against movement relative to the body tissue 72. Thus, the outer corner portions 22, 24 and 26 of the anchor 10 become embedded in the body tissue 72. The flat outer side surface areas 28 and 32 of the anchor are pressed against the body tissue to further stabilize the anchor.

With the passage of time, the body tissue tends to grow into the recess 78 and the space caused by moving the anchor 10 from the position shown in FIG. 2 through the position shown in FIG. 4 to the position shown in FIG. 5. As this occurs, the body tissue grows into engagement with the flat outer side surface area 30 of the anchor to further stabilize the anchor. Although the anchor 10 is very stable in the body tissue 72, the anchor can be removed from the body tissue in the same manner as is disclosed in the aforementioned U.S. patent application Ser. No. 08/062,295 filed May 14, 1993 of which this application is a continuation-in-part.

Anchor Guide and Pusher Members—Second Embodiment

In the embodiment of the invention illustrated in FIGS. 1–6, the anchor 10 is randomly oriented relative to the guide member 82. As the anchor 10 emerges from the guide member 82, the force applied against the anchor by tensioning the suture 12 results in the suture moving along an inner side surface area 48, 50 or 52 of the anchor into engagement with one of the inner corner portions 40, 42 and 44. As this occurs, the anchor moves relative to the pusher member 112 to an orientation in which the tapered end portion 116 of the pusher member 112 applies a concentrated force against a portion of the anchor opposite from the inner corner portion engaged by the suture 12. For example, if the suture 12 engages the inner corner portion 40, as shown in FIG. 4, the pusher member 112 applies a concentrated force against the side wall 58 adjacent to the outer corner portions 24 and 26.

It is contemplated that it may be desired to orient the anchor 10 relative to the body tissue 72 before the anchor begins to move into the recess 78. In the embodiment of the invention illustrated in FIGS. 7–10, the tubular guide member is constructed so as to retain the anchor in a selected orientation relative to the guide member as the anchor moves axially through the guide member. In addition, the pusher member is constructed so as to apply a concentrated force against a selected portion of the anchor. Since the embodiment of the invention illustrated in FIGS. 7–10 is generally similar to the embodiment of the invention illustrated in FIGS. 1–6, similar numerals will be utilized to designate similar components, the suffix letter "a" being associated with the numerals of FIGS. 7–10 to avoid confusion.

A tubular guide member 82a (FIG. 7) has a cylindrical outer side surface 88a and a cylindrical inner side surface 92a. In addition, the guide member 82a has a linear locating rib 142 which orients the anchor 10a in the guide member 82a. The locating rib 142 extends axially along the inner side 92a of the guide member 82a for the entire length of the guide member. A longitudinal central axis of the locating rib 142 extends parallel to a longitudinal central axis of the guide member 82a.

The locating rib 142 has a flat inwardly facing locating surface 144. The flat locating surface 144 is disposed in a plane which forms a chord to the cylindrical inner side surface 92a of the guide member 82a. The plane in which the locating surface 144 is disposed, extends parallel to the longitudinal central axis of the guide member 82a. The locating surface 144 has an axial extent which is the same as the axial extent of the guide members 82a.

When an anchor 10 is in the orientation shown in FIG. 7, the locating surface 144 engages the flat outer side surface area 30a on the anchor 10a to position the anchor in a predetermined orientation relative to the guide member 82a. The corner portion 22a of the anchor 10a is disposed diametrically across from the locating surface 144. Of course, the anchor 10a could be positioned relative to the tubular guide member 82a with the flat locating surface 144 in abutting engagement with any one of the flat outer side surface areas 28a, 30a or 32a on the anchor.

The corner portions 22a, 24a and 26a (FIG. 7) of the anchor 10a engage the cylindrical inner side surface 92a of the guide member 82a to hold the anchor 10a in alignment with a longitudinal central axis of the guide member 82a. The locating surface 144 engages the flat outer side surface area 30a on the anchor 10a to hold the anchor in a predetermined orientation relative to the longitudinal central axis of the guide member 82a. Thus, the locating surface 144 engages the flat outer side surface 30a on the anchor 10a to prevent rotation of the anchor about its longitudinal central axis relative to the guide member 82a. The longitudinal central axis of the anchor 10a is coincident with the longitudinal central axis of the guide member 82a.

The location of the anchor 10a relative to the body tissue into which it is to be inserted can be selected by a surgeon before inserting the anchor. Thus, the outer corner portion 22a of the anchor 10a is diametrically across the guide member 82a from the locating surface 144. At this time, the corner portion 22a of the anchor 10a has a longitudinal central axis which is located in a plane which contains the longitudinal central axis of the locating rib 142. Therefore, by selecting the orientation of the locating rib 142 relative to the body tissue, the surgeon can select the orientation of the outer corner portion 22a of the anchor relative to the body tissue.

When the anchor 10a is installed in body tissue to anchor the suture 12a, in the manner shown in FIGS. 5 and 6 for the anchor 10, the longitudinal central axis of the corner portion 22a of anchor 10a is still disposed in the plane containing the parallel longitudinal central axes of the guide member 82a and the locating rib 142. The longitudinal central axis of the anchor 10a is also disposed in the plane containing the longitudinal central axes of the guide member 82a and the locating rib 142. However, when the anchor 10a is installed in body tissue, in the manner shown in FIGS. 5 and 6 for the anchor 10, the longitudinal central axes of the corner portion 22a and anchor 10a extend perpendicular to the parallel longitudinal central axes of the guide member 82a and locating rib 142.

A pusher member 112a (FIGS. 8 and 9) cooperates with the guide member 82a to apply force against the anchor 10a at locations which are opposite from the outer corner portion 22a and are adjacent to opposite longitudinally extending side surfaces 146 and 148 (FIG. 7) on the locating rib 142. The side surfaces 146 and 148 extend perpendicular to the locating surface 144. The side surfaces 146 and 148 extend parallel to each other and are spaced apart by a distance which is substantially less than the distance between the corner portions 24a and 26a of the anchor 10a.

The pusher member 112a is a cylindrical tubular member having a tapered end portion 116a (FIG. 8). The tubular pusher member 112a has a radially extending slot 150 (FIG. 9) which extends throughout the length of the pusher member and receives the locating rib 142. Opposite side surfaces 151 and 152 of the slot 150 extend parallel to each other and engage opposite side surfaces 146 and 148 on the locating rib 142. Thus, the locating rib 142 cooperates with the slot 150 to orient the pusher member 112a relative to the guide member 82a. Since the anchor 10a is also oriented relative to the guide member 82a by the locating rib 142, the locating rib is effective to orient the pusher member 112a relative to the anchor.

The pusher member 112a has a tapered leading or lower (as viewed in FIG. 8) end surface 128a which applies force against the anchor 10a at locations adjacent to opposite sides of the locating rib 142 in the tubular guide member 82a. The manner in which the end surface 128a on the pusher member 112a applies force against the anchor 10a is indicated schematically in FIG. 7 by the arrows 154 and 156. The arrows 154 and 156 extend parallel to the longitudinal central axis of the locating rib 142 and to the longitudinal central axis of the anchor 10a.

The pusher member force represented by the arrows 154 and 156 is applied against the trailing end surface area 68a on the side wall 58a (FIG. 7) of the anchor 10a opposite from the outer corner portion 22a. Thus, the pusher member 112a applies a force which is concentrated against the same side wall 58a of the anchor as is engaged by the locating surface 144 on the locating rib 142. This results in the pusher member 112a applying force against the trailing end surface 68a of the anchor 10a at locations which are selected by selecting the orientation of the anchor in the guide member 82a.

When the anchor 10a is to be installed in body tissue, the tubular guide member 82a is positioned in a selected orientation relative to the body tissue. Thus, the open lower end 96a (FIG. 10) of the guide member 82a is inserted into a recess in the body tissue, in the manner illustrated in FIG. 2 for the guide member 82, with the locating rib 142 at a location where it is desired to have the outer corner portion 22a of the anchor 10a embedded in the body tissue.

The suture 12a (FIG. 10) is inserted through the central passage 18a in the anchor 10a. Thus, the portion 104a of the suture 12a extends through the passage 18a in the anchor 10a and the portion 108a of the suture 12a extends along the outer side surface 32a of the anchor. The suture is also inserted through the central passage 114a (FIG. 8) in the pusher member 112a.

The anchor 10a is then positioned in the guide member 82a with the flat outer side surface area 30a (FIG. 7) on the anchor in abutting engagement with the flat locating surface 144 on the locating rib 142. The portion 108a of the suture will extend through the channel 100a formed between the inner side surface 92a of the guide member 82a and the outer side of the anchor 10a.

The pusher member 112a is then inserted into the tubular guide member 82a with the portions 104a and 108a of the suture 12a extending through the cylindrical passage 114a in the tubular pusher member. The locating rib 142 extends radially through the slot 150 formed in the pusher member 112a. The side surfaces 151 and 152 of the slot 150 (FIG. 9) engage opposite side surfaces 146 and 148 on the locating rib 142). Engagement of the locating rib 142 with the slot 150 in the pusher member 112a orients the pusher member 112a relative to both the anchor 10a and the guide member 82a.

The lower or leading end surface 128a (FIG. 8) on the pusher member 112a engages the upper end surface of the side wall 58a (FIG. 7) of the anchor 10a adjacent to opposite sides of the locating rib 142. Thus, when the pusher member 112a is pressed against the anchor 10a, the end surface 128a on the pusher member 112a applies force against the trailing end surface 68a of the anchor 10a at the side wall 58a, in the manner indicated by the arrows 154 and 156 in FIG. 7.

The force applied against the trailing end surface 68a of the anchor 10a by the pusher member 112a moves the anchor axially downward (as viewed in FIG. 7) through the guide member 82a until a leading end surface 66a (FIG. 10) on the anchor emerges from the open lower (as viewed in FIG. 10) end 92a of the guide member 82a. During this movement of the anchor 10a through the tubular guide member 82a, both the anchor and the pusher member 112a are maintained in a predetermined orientation relative to the guide member by the locating rib 142. The locating rib 142 cooperates with the pusher member 112a and the anchor 10a to retain them against rotation relative to each other about the central axis of the guide member 82a.

Figure 10:
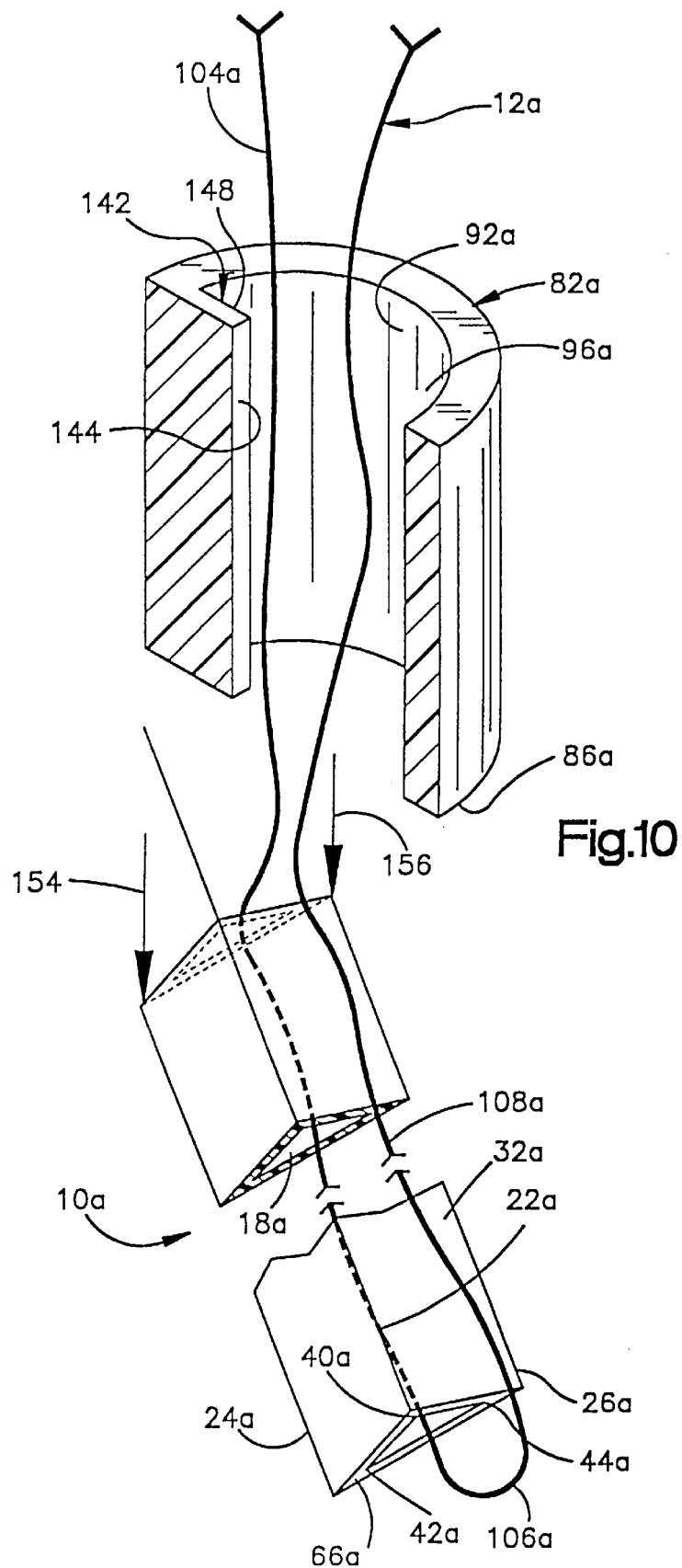
FIG. 10 is a schematicized cross-sectional view, illustrating the relationship of the anchor to the tubular guide member of FIG. 7 as the anchor moves out of the tubular guide member into body tissue.

As the anchor 10a begins to emerge from the lower (as viewed in FIG. 10) end portion 86a of the tubular guide member 82a, the force applied against the trailing end surface 68a of the anchor by the pusher member 112a applies a torque to the anchor which tends to rotate the anchor in a counterclockwise direction (as viewed in FIG. 10). As this occurs, the suture 12a is tensioned to apply a force against the inner corner portion 40a of the anchor 10a adjacent to the leading end surface 66a of the anchor. The forces result in the anchor being rotated in a counterclockwise direction as viewed in FIG. 10.

Once the trailing end of the anchor 10a has moved clear of the tubular guide member 82a, the force applied against the leading end surface 66a of the anchor 10a by the portion 106a of the suture 12a moves the anchor 10a toward the left (as viewed in FIG. 10). Therefore, the anchor 10a moves to a position in which it extends diametrically across the open lower end portion 92a of the guide member 82a. This results in the anchor 10a being installed in body tissue in a position similar to that shown for the anchor 10 in FIGS. 5 and 6.

Continued pulling or tensioning of the suture 12a results in the corner portion 22a of the anchor becoming embedded in the body tissue and the outer side surfaces 28a and 32a of the anchor applying force against the body tissue. At this time, the outer corner portions 24a and 26a cooperate with the body tissue to further stabilize the anchor 10a. Once the anchor 10a has been moved into position in the body tissue, both the guide member 82a and the pusher member 112a are withdrawn from the body tissue.

In the embodiment of the invention illustrated in FIGS. 7–10, the locating rib 142 positions the anchor relative to the guide member 82a. However, it is contemplated that many different arrangements of locating surfaces could be provided on the guide member to locate the anchor relative to the guide member. For example, the guide member 82a could be formed with a configuration corresponding to the configuration of a segment of a circle. If this was done, the portion 108a of the suture 12a would be disposed adjacent to the arcuate portion of the guide member while the opposite outer corner portion of the anchor would be engaged by the apex of the guide member. If desired, the guide member could have a polygonal cross-sectional configuration corresponding to the polygonal cross-sectional configuration of the anchor. If this is done, a groove in the guide member could be used as a channel to receive the portion 108a of the suture 12a.

Anchor—Second Embodiment

Figure 11:
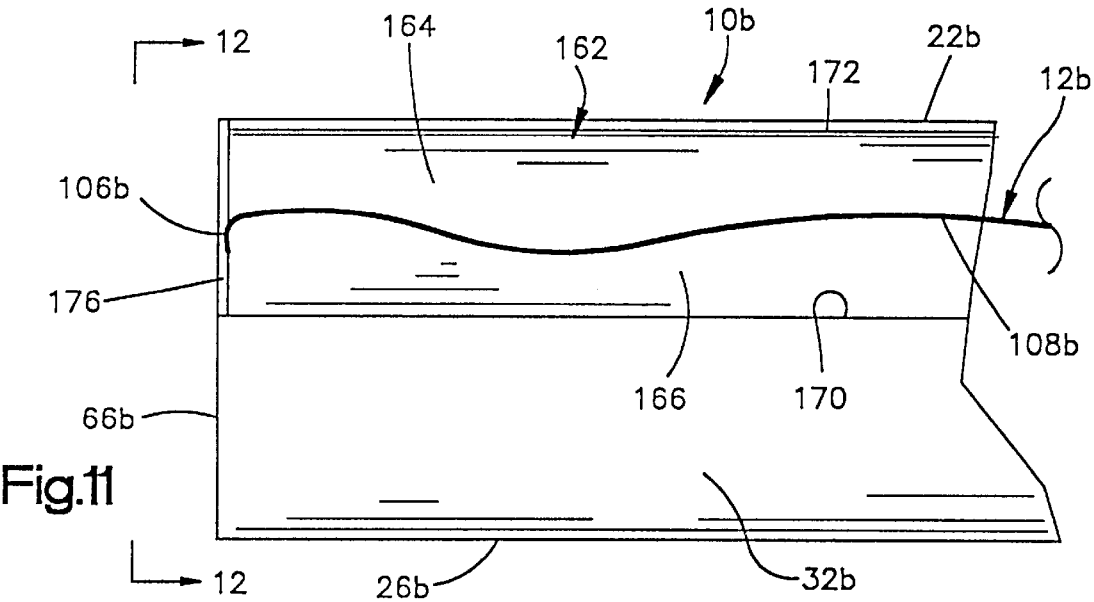
FIG. 11 is a side elevational view of an embodiment of the anchor of FIG. 1 having a groove to receive the suture.

It is contemplated that during use of the anchor 10 of FIGS. 1–6, it may be desired to protect the suture 12 from engagement with surfaces in the environment in which the anchor is used. In the embodiment of the anchor illustrated in FIGS. 11 and 12, grooves are provided to receive the suture to protect the suture. Since the embodiment of the anchor illustrated in FIGS. 11 and 12 is generally similar to the embodiment of the invention illustrated in FIGS. 1–6, similar numerals will be utilized to designate similar components, the suffix letter "b" being associated with the numerals of FIGS. 11 and 12 to avoid confusion.

An anchor 10b has outer corner portions 22b, 24b and 26b which interconnect flat outer side surface areas 28b, 30b and 32b. A central passage 18b extends through the anchor. The anchor 10b has the same configuration as the anchor 10 of FIG. 1.

In accordance with a feature of this embodiment of the invention, the anchor 10b has a groove 162 (FIG. 11) in which the suture 12b is received. The groove 162 has a longitudinally extending main portion 164 which is disposed inwardly from the flat outer side surface 32b of the anchor 10b. The main portion 164 of the groove 162 has a flat bottom surface 166 which extends parallel to the flat outer side surface area 32b and extends between axially opposite ends of the anchor 10b. The main portion 164 of the groove 162 receives the portion 108b of the suture 12b which extends along the outside of the anchor.

Figure 12:
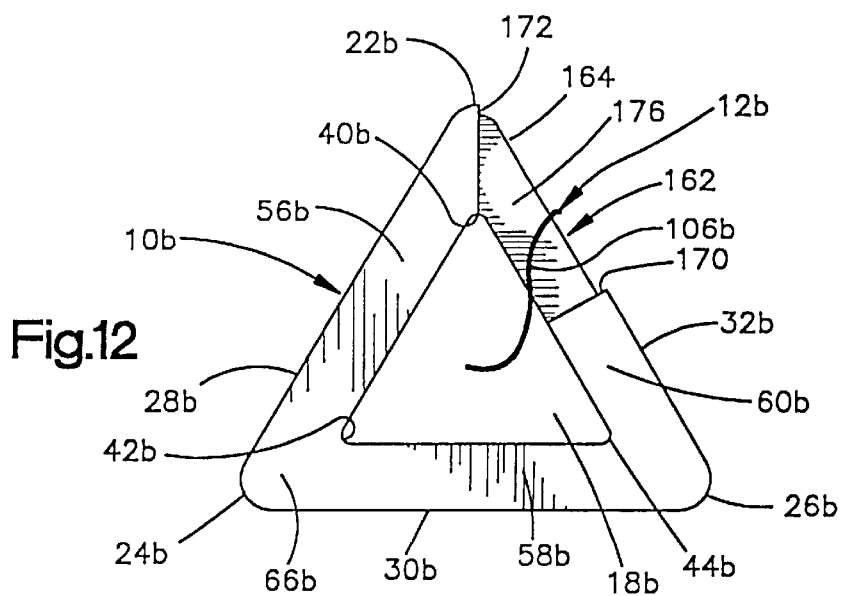
FIG. 12 is an end view, taken generally along the line 12—12 of FIG. 11, further illustrating the construction of the groove and the relationship of the suture to the groove.

The main portion 164 of the groove 162 has a flat longitudinally extending side surface 170 which is disposed in a central portion of the flat outer side surface 32b and a flat longitudinally extending side surface 172 which is disposed in a central portion of the outer corner portion 22b (FIG. 12). This enables the portion 108b (FIG. 11) of the suture 12b to move from a position adjacent to the central portion of the flat outer side surface 32b to the outer corner portion 22b as the inner portion of the suture moves into engagement with the inner corner portion 40b (FIG. 12) of the anchor 10b. Thus, as the anchor 106 is rotated and moved into position relative to the end of the guide member in the manner shown in FIGS. 4 and 5 for the anchor 10, the portion 108b of the suture 12b will move sidewardly, that is in a direction transverse to the longitudinal central axis of the main portion 164 of the groove 162, into engagement with the longitudinally extending side surface 172 of the groove. This occurs as the portion of the suture which extends through the passage 18b in the anchor 10b moves into engagement with the inner corner portion 40b of the anchor.

In addition, the groove 162 has an end portion 176 which extends transversely to the main portion 164 of the groove 162 and extends across the end surface 66b of the anchor 10b. The end portion 176 of the groove 162 extends from a central portion of an end of the side wall 60b to the inner and outer corner portions 40b and 22b. The end portion 176 of the groove 162 receives the portion 106b of the suture 12b to protect the suture. Since the end portion 176 of the groove extends from the central portion of the side wall 60b to the outer corner portion 22b, the portion 106b of the suture can move to a location extending between the inner corner portion 40b and the outer corner portion 22b as the anchor is moved from the orientation shown in FIG. 4 to the orientation shown in FIG. 5 for the anchor 10.

Although the groove 162 has been illustrated herein as having both the main portion 164 and the end portion 176, it is contemplated that the groove 162 could have either just the main portion 164 or the end portion 176 if desired. It is also contemplated that the groove 162 could have a configuration other than the configuration illustrated herein.

Plural Anchors

In the embodiment of the invention illustrated in FIGS. 1–6, a single anchor 10 is used to secure the suture 12 in body tissue. In the embodiment of the invention illustrated in FIGS. 13–16, a plurality of anchors are used to secure a suture in body tissue. Since the embodiment of the invention illustrated in FIGS. 13–16 is generally similar to the embodiment of the invention illustrated in FIGS. 1–6, similar numerals will be utilized to designate similar components, the suffix letter "c" being associated with the numerals of FIGS. 13–16 to avoid confusion.

In accordance with a feature of this embodiment of the invention, a pair of anchors 182 and 184 (FIG. 13) are used to secure a suture 12c in body tissue. However, a greater number of anchors could be used if desired. The anchors 182 and 184 both have the same general construction as the anchor 10 of FIGS. 1–6. However, the trailing anchor 182 has a tapered leading end portion 186. If desired, the anchors 182 and 184 could have a construction which is different from the construction of the anchor 10.

The tapered leading end portion 186 of the trailing anchor 182 extends from an outer corner portion 22c of the anchor 182 to an outer side surface 30c on a side wall 58c and to the corner portions opposite from the corner portion 22c of the anchor 182. The outer side surface area 30c has a flat rectangular configuration. The tapered leading end portion 186 of the anchor 182 includes a flat leading end surface 66c which is disposed in a plane which is skewed at an acute angle to a trailing end surface 68c. Other than having the tapered leading end portion 186, the construction of the anchor 182 is the same as the construction of the anchor 10 of FIGS. 1–6.

The leading anchor 184 has the same construction as the anchor 10 of FIGS. 1–6. Thus, the leading anchor 184 has a leading end surface 66c which is parallel to the trailing end surface 68c. The leading and trailing end surfaces 66c and 68c of the anchor 184 extend perpendicular to a longitudinal central axis of the suture.

Although it is preferred to use anchors 182 and 184 having the same configuration as the anchor 10 of FIGS. 1–6, the anchors 182 and 184 could have a configuration which is different than the configuration of the anchor 10. For example, the anchors 182 and 184 could have a cylindrical configuration or any of the other anchor configurations disclosed in the aforementioned U.S. patent application Ser. No. 08/062,295 filed May 14, 1993 of which this application is a continuation-in-part. However, the anchor corresponding to the anchor 182 and having any one of these constructions may be provided with a tapered leading end portion.

Although it is preferred to form the leading anchor 184 with a trailing end surface 68c which extends perpendicular to the central axis of the anchor, the trailing end portion of the leading anchor 184 could be tapered in a manner similar to the tapered leading end portion 186 of the trailing anchor 182. If the trailing end portion of the anchor 184 is tapered, the leading end portion of the anchor 182 could extend perpendicular to the central axis of the anchor 182 or could be tapered in a manner similar to that shown in FIG. 13.

When the anchors 182 and 184 are to be used to secure the suture 12c into bone 72c or other body tissue, a cylindrical recess 78c may be formed in the body tissue. A tubular cylindrical guide member 82c is inserted into the recess 78c in the manner illustrated in FIG. 13. Although the tubular guide member 82c has the same construction as the guide member 82 of FIGS. 2–6, a guide member having a different construction could be used if desired.

The suture 12c is inserted through central passages 18c in the anchors 182 and 184. This results in the two anchors 182 and 184 being strung together on the suture 12c. A portion 104c (FIG. 13) of the suture 12c extends through the central passage 18c in the anchor 182 and through the central passage 18c in the anchor 184. A portion 106c of the suture 12c extends across the leading end surface 66c of the leading anchor 184. A portion 108c of the suture 12c extends along the outside of the two anchors 182 and 184.

After the anchors 182 and 184 have been strung on the suture 12c, the anchors 182 and 184 are positioned in the tubular guide member 82c. Corner portions of the anchors 182 and 184 engage a cylindrical inner side surface 92c of the guide member 82c. Thus, the corner portions of the anchors 182 and 184 engage the inner side surface 92c of the guide member 82c in the same manner as in which the corner portions 22, 24 and 26 of the anchor 10 engage the inner side surface 92 of the tubular guide member 82 (FIG. 3).

The anchors 182 and 184 are positioned in the cylindrical guide member 82c with the corner portions of the anchors aligned with each other and with the anchors in a coaxial relationship with each other. The anchors 182 and 184 are also positioned in the guide member 82c with the anchors in a coaxial relationship with each other and with the guide member. A knife edge end 190 of the tapered leading end portion 186 of the anchor 182 is disposed in engagement with the trailing end surface 68c of the anchor 184 along the side wall 58c of the anchor 184. The knife edge end 190 of the tapered leading end portion 186 of the anchor 182 has a configuration similar to the configuration of a cutting portion of a chisel. The knife edge end 190 extends along the side wall 58c of the anchor 182 between corner portions at opposite ends of the side wall, that is, between corner portions corresponding to the corner portions 24 and 26 (FIG. 3) of the anchor 10. Thus, force is transmitted from the trailing anchor 182 to the leading anchor 184 along the entire width of the trailing end surface of the side wall 58c of the anchor 184.

A cylindrical tubular pusher member 112c is inserted into the guide member 82c and applies force to the trailing end surface 68c of the trailing anchor 182. The pusher member 112c has a flat circular leading end surface 126c which is disposed in a plane extending perpendicular to a longitudinal central axis of the pusher member 112c. Thus, the pusher member 112c of FIG. 13 does not have a tapered open end portion in the same manner as does the pusher member 112 of FIGS. 2 and 4. However, if desired, the pusher member 112c could be provided with a tapered open end portion having a configuration similar to the configuration of the tapered open end portion 116 of the pusher member 112 (FIGS. 2 and 4).

The circular leading end surface 126c of the pusher member 112c engages the trailing end surface 68c of the trailing anchor 182 at each of the three corner portions of the anchor. This results in the trailing anchor 182 being pushed straight down (as viewed in FIG. 13) by the pusher member 112c. The pusher member 112c does not apply torque to the trailing anchor 182. This is because the force applied to the trailing end surface 68c of the anchor 182 by the pusher member 112c is balanced about the central axis of the anchor.

Although the pusher member 112c does not apply torque to the trailing anchor 182, the trailing anchor 182 is effective to apply torque to the leading anchor 184. This is because force is transmitted from the trailing anchor 182 through the tapered leading end portion 186 of the trailing anchor 182 to the leading anchor 184. The force transmitted from the trailing anchor 182 to the leading anchor 184 is concentrated along the width of the side wall 58c of the leading anchor by the knife edge end 190 of the trailing anchor. This concentrated force is offset from the longitudinal central axis of the leading anchor 184. Therefore, the trailing anchor 182 applies torque to the leading anchor 184 tending to rotate the leading anchor in a counterclockwise direction, as viewed in FIG. 13, about an axis which extends through the location where the knife edge end 190 of the trailing anchor 182 engages the side wall 58c of the leading anchor 184. Thus, the torque applied to the leading anchor 184 by the trailing anchor 182 tends to rotate the leading anchor about an axis which extends parallel to the flat outer side surfaces 30c of the anchors and which extends along a linear line of engagement of the knife edge end 190 of the trailing anchor with the trailing end surface 68c of the leading anchor.

Since the three outer corner portions of the leading anchor 184 are disposed in engagement with the cylindrical inner side surface 92c of the guide member 82c, in the manner illustrated in FIG. 3 for the anchor 10, the leading anchor 184 is restrained against rotational movement under the influence of torque transmitted from the trailing anchor 182 to the leading anchor 184. Thus, the leading anchor 184 is moved straight downward (as viewed in FIG. 13) under the influence of the force transmitted from the trailing anchor 182 to the leading anchor. The leading end surface 66c of the leading anchor 184 applies force against the portion 106c of the suture 12c to pull the suture downward in the guide member 82c.

As the anchors 182 and 184 are moved downward (as viewed in FIG. 13) together along the guide member 82c under the influence of forces applied against the trailing anchor 182 by the pusher member 112c, the leading anchor 184 moves through the open lower end portion 86c of the guide member 82c. As this occurs, the concentrated force applied against the trailing end surface 68c of the leading anchor 184 by the tapered knife edge end portion 186 of the trailing anchor 182 causes the leading anchor to rotate in a counterclockwise direction, in the manner indicated by the arrow 140c in FIG. 14. This results in the leading anchor 184 rotating about an axis which extends through the location where the knife edge end 190 of the trailing anchor 182 engages the portion of the trailing end surface 68c of the leading anchor 184 disposed on the trailing end of the side wall 58c of the leading anchor 184.

As the leading anchor 184 is being rotated under the influence of the torque applied against it by the trailing anchor 182, the trailing anchor continues to move straight downward (as viewed in FIG. 14) along the tubular guide member 82c. As the leading anchor 184 is rotated in a counterclockwise direction, in the manner indicated by the arrow 140c in FIG. 14, the leading end 66c of the leading anchor moves rightward into the relatively soft cancellous bone tissue 76c. The outer corner portion 22c of the anchor 184 is leading. The wedge-shaped configuration of the outer corner portion 22c of the leading anchor 184 facilitates movement of the leading anchor 184 in the cancellous bone tissue.

As this is occurring, the suture 12 is tensioned by pulling on the two portions 106c and 108c of the suture. This pulls the portion 106c of the suture against the leading end surface 66c of the leading anchor 184. The force applied by the suture 12c to the leading end surface 66c of the leading anchor 184 urges the leading anchor upward and toward the left (as viewed in FIG. 14) toward the tapered leading end portion 186 of the trailing anchor 182. The counterclockwise (as viewed in FIG. 14) rotation of the leading anchor 184 continues until the trailing end surface 68c on the leading anchor engages the leading end surface 66c on the trailing anchor 182.

After the trailing end surface 68c on the leading anchor 184 has engaged the leading end surface 66c on the trailing anchor 182, the pusher member 112c pushes the trailing end surface 68c of the trailing anchor 182 out of the guide member 82c. As this occurs, the outer corner portions of the trailing anchor 182 move out of engagement with the cylindrical inner side surface 92c of the guide member 82c. Force transmitted from the suture 12c through the leading anchor 184 to the trailing anchor 182 causes the trailing anchor to rotate and move leftward toward the position shown in FIG. 15.

As this is occurring, the leading anchor 184 continues to rotate under the influence of the force applied against the leading anchor by the suture 12c. As the suture 12c is tensioned, the two anchors 182 and 184 are rotated together through the position shown in FIG. 15 to the position shown in FIG. 16. When the anchors 182 and 184 reach the position shown in FIG. 16, the outer corner portions 22c of the anchors engage the lower end surface 86 of the guide member 82c and are embedded in the soft cancellous bone tissue.

The force applied against the two anchors 182 and 184 by tensioning the suture 12c presses the leading end surface 66c on the tapered leading end portion 186 of the trailing anchor 182 firmly against the trailing end surface 68c on the anchor 184. At this time, the flat outer major side surfaces on the anchors 182 and 184 press against the soft cancellous bone tissue and the outer corner portions of the anchors 182 and 184 are engaged by the soft cancellous bone tissue to stabilize the anchors 182 and 184 in the same manner as previously explained in conjunction with the embodiment of the invention illustrated in FIGS. 1–6. Therefore, the anchors 182 and 184 are disposed in stable abutting engagement with each other and are held against movement relative to the bone tissue 72c.

When the anchors 182 and 184 have been installed in the body tissue 72c, as shown in FIG. 16, the guide member 82c and pusher member 112c are withdrawn from the body tissue. At this time, the anchors 182 and 184 have longitudinal central axes which are skewed relative to each other and slope upward (as viewed in FIG. 16) in opposite directions toward the outer side surface of the body tissue 72c. Tensioning of the suture 12c presses the leading end surface 66c on the trailing anchor 182 firmly against the trailing end surface 68c on the leading anchor 184. The two anchors 182 and 184 become wedged together and span the opening in the body tissue 72c to strongly resist pulling out of the anchors 182 and 184 and the suture 12c from the body tissue 72c.

Since the anchors 182 and 184 slope upward (as viewed in FIG. 16) toward the outer side surface of the body tissue 72c and away from each other, pulling on the suture 12c results in the anchors becoming wedged even more firmly in the body tissue. The fore applied against the inner side surfaces of the anchors 182 and 184 by pulling on the suture 12c tends to further embed the trailing end portion of the trailing anchor 182 and the leading end portion of the leading anchor 184 in the body tissue. Pulling on the suture 12c tends to center the two anchors 182 and 184 across the opening through which they were inserted into the body tissue 72c.

In the embodiment of the invention illustrated in FIGS. 13–16, the anchors 182 and 184 both have the same general polygonal construction as the anchor 10 of FIG. 1. However, it is contemplated that the anchors 182 and 184 could have a different construction if desired. Thus, the anchor 182 and/or the anchor 184 could have a cylindrical construction.

Plural Anchors—Guide and Pusher Members

In the embodiment of the invention illustrated in FIGS. 13–16, the anchors 182 and 184 are randomly oriented relative to the guide member 82c. It is contemplated that it may be desired to orient the anchors 182 and 184 relative to the body tissue 72c before the anchors begin to move into the recess 78. In the embodiment of the invention illustrated in FIG. 17, the guide member is constructed so as to retain the anchors in a selected orientation relative to the guide member as the anchors move axially through the guide member. In addition, the pusher member is constructed so as to apply a concentrated force against a selected portion of the anchor. Since the embodiment of the invention illustrated in FIG. 17 is generally similar to the body of the invention illustrated in FIGS. 13–16 and since the guide members and pusher members are constructed in a manner which is generally similar to the embodiment of the invention illustrated in FIGS. 7–10, similar numerals will be utilized to designate similar components, the suffix letter "d" being associated with the numerals of FIG. 17 to avoid confusion.

In the embodiment of the invention illustrated in FIG. 17, the tubular guide member 82d has a cylindrical outer side surface 88d with a cylindrical inner side surface 92d. In addition, the guide member 82d has a locating rib 142d which orients the anchors 182d and 184d in the guide member 82d. The locating rib 142d extends along the inner side surface 92d of the guide member 82d for the entire length of the guide member.

The locating rib 142d has a flat inwardly facing locating surface 144d. The flat locating surface 144d is disposed in a plane which forms a chord to the cylindrical inner side surface 92d of the guide member 82d. The locating surface 144d has an axial extent which is the same as the axial extent of the guide member 82d.

The locating surface 144d engages the flat outer side surface area 30d on the trailing anchor 182d and the flat outer side surface area 30d on the leading anchor 184d. This enables the locating surface 144d to position the anchors 182d and 184d in a predetermined orientation relative to the guide member 82d. Thus, the corner portions 22d of the anchors 182d and 184d are disposed diametrically across from the locating surface 144d. The locating surface 144d engages the flat outer side surface areas 30d on the anchors 182d and 184d to hold the anchors in a predetermined orientation relative to a longitudinal central axis of the guide member 82d.

A pusher member 112d cooperates with the guide member 82d to apply force against the trailing anchor 182d at the corner portions of the trailing anchor. The pusher member 112d is a cylindrical tubular member having a radially extending slot 150d which extends throughout the length of the pusher member and receives the locating rib 142d. The manner in which the pusher member 112d cooperates with the guide member 82d is the same as previously explained in conjunction with the embodiment of the invention illustrated in FIGS. 7–10. However, the pusher member 112d does not have a tapered leading end portion corresponding to the tapered leading end portion 116a (FIG. 8) of the pusher member 112a. If desired, the pusher member 112d could be provided with a tapered leading end portion.

The pusher member 112d cooperates with the trailing anchor 182d and leading anchor 184d and the guide member 82d to position the anchors 182d and 184d in the same manner as previously explained in conjunction with the embodiment of the invention illustrated in FIGS. 13–16. By using the locating rib 182d, a surgeon can determine the orientation of the anchors in the body tissue 72d by positioning the guide member 82d relative to the body tissue 72d in an orientation corresponding to the desired orientation of the anchors 182 and 184d to the body tissue.

Plural Anchors—Guide Member—Third Embodiment

In the embodiment of the invention illustrated in FIG. 17, the guide member 182d is provided with a locating rib 142d to locate the anchors 182d and 184d relative to the body tissue 72d. In the embodiment of the invention illustrated in FIG. 18, the guide member is provided with a plurality of longitudinally extending grooves which locate the anchors relative to the body tissue. Since the embodiment of the invention illustrated in FIG. 18 is generally similar to the body of the invention illustrated in FIGS. 13–17, similar numerals will be utilized to designate similar components, the suffix letter "e" being associated with the numerals of FIG. 18 to avoid confusion.

The guide member 82e has a cylindrical inner side surface 92e. In accordance with a feature of this embodiment of the invention, the guide member 82e is provided with three spaced-apart and parallel longitudinally extending locating grooves 202, 204, and 206 (FIG. 18). The locating grooves 202, 204, and 206 extend axially throughout the length of the guide member 82e and are spaced equal arcuate distances apart about the cylindrical inner side surface 92e of the guide member 82e. Thus, the locating grooves 202, 204 and 206 are spaced approximately 120° apart.

The corner portions 22e, 24e and 26e on the anchor 182e engage the guide grooves 202, 204, and 206 in the manner illustrated in FIG. 18. Although only the corner portions 22e, 24e and 26e for the trailing anchor 182e are shown in FIG. 18, it should be understood that the leading anchor, corresponding to the leading anchor 184 of FIG. 13, has corner portions which engage the guide grooves 202, 204, and 206 in the same manner as do the corner portions of the trailing anchor.

The pusher member has not been shown in FIG. 18, it is contemplated that a cylindrical pusher member, similar to the pusher member 112 of FIGS. 8 and 9 may be used to apply force against the trailing end surface 68e of the anchor 182e (FIG. 18).

Plural Anchors—Second Embodiment

Figure 20:
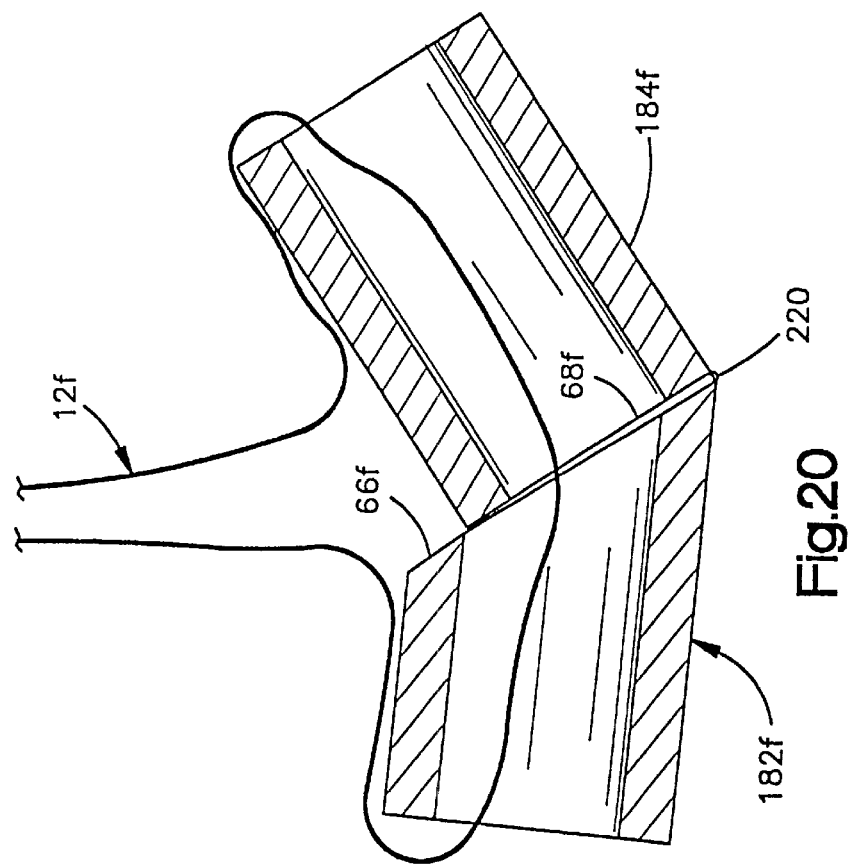
FIG. 20 is a schematicized illustration depicting the manner in which the connector section is resiliently deformed by tensioning the suture to urge the anchors into engagement with body tissue in a manner similar to that illustrated in FIG. 16.
Figure 19:
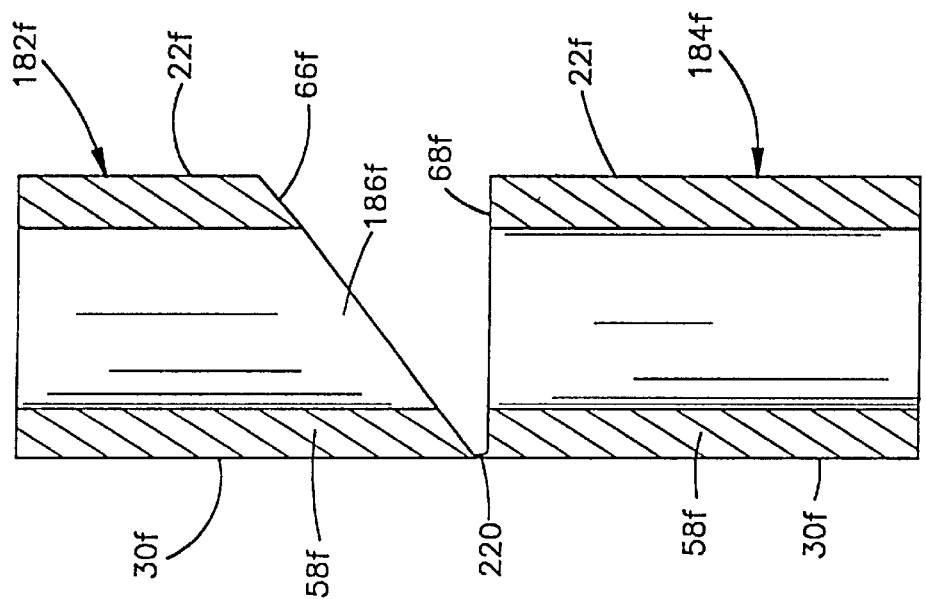
FIG. 19 is an enlarged sectional view illustrating the relationship between a pair of anchors which are interconnected by a connector section.

In the embodiment of the invention illustrated in FIGS. 13–16, the anchors 182 and 184 are formed separately from each other. This requires a surgeon to properly align and thread the anchors on the suture 12c in the manner illustrated in FIG. 13. In the embodiment of the invention illustrated in FIGS. 19 and 20, a connector portion is provided to interconnect the two anchors. The connector portions retains the anchors in the proper orientation relative to each other and facilitate threading of the suture through the two anchors. Since the embodiment of the invention illustrated in FIGS. 19 and 20 is generally similar to the embodiment of the invention illustrated in FIGS. 13–16, similar numerals will be utilized to designate similar components, the suffix letter "f" being used in conjunction with the numerals of FIGS. 19 and 20 to avoid confusion.

An anchor 182f (FIG. 19) has the same construction as the anchor 182 of FIGS. 13–16. An anchor 184f has the same construction as the anchor 184 of FIGS. 13–16. In accordance with a feature of this embodiment of the invention, the anchors 182f and 184f are interconnected by a connector 220 which extends between the two anchors 182f and 184f. The connector 220 has a length which is coextensive with the width of side walls 58f of the anchors 182f and 184f.

The anchors 182f and 184f have side walls 58f with flat outer side surface areas 30f which are disposed in a common plane. In addition, the anchors 182f and 184f have outer corner portions 22f which are axially aligned with each other. The outer side surface areas 30f on the side walls 58f of the anchors 182f and 184f are maintained in alignment with each other by the connector 220. In addition, the connector 220 maintains the outer corner portions 24f on the anchors 182f and 184f in alignment with each other.

Since the two anchors 182f and 184f are interconnected by the connector 220, the tapered leading end portion 186f of the trailing anchor 182f always faces toward the trailing end surface 68f of the leading anchor 184f. Therefore, when a suture 12f (FIG. 20) is threaded through the anchors 182f and 184f, the anchors are always in the proper orientation relative to each other.

When the anchors 182f and 184f are installed in body tissue, in the manner illustrated in FIGS. 13–16 for the anchors 182 and 184, the connector 220 is deformed to enable the leading anchor 184f to move from the orientation shown in FIG. 19 to the orientation shown in FIG. 20 relative to the anchor 182f. Thus, when the anchors 182f and 184f have been moved to their installed positions relative to each other, in the manner illustrated in FIG. 20, the connector 220 is bent so that the leading end surface 66f on the anchor 182f and the trailing end surface 68f on the anchor 184f are disposed in abutting engagement.

The connector 220 is a web which extends along the leading end portion of the outer side surface 30f in the side wall 58f of the anchor 182f and along a trailing portion of the outer side surface 30f of the side wall 58f of the anchor 184f. The relatively thin web forming the connector 220 is integrally formed with the two anchors 182f and 184f. Thus, the two anchors 182f and 184f are formed as one piece having the configuration of an equilateral triangular prism. The leading end surface 66f on the anchor 182f and the trailing end surface 68f on the anchor 184f are formed by making a notch in the one piece prism. The notch does not extend completely through the side walls 58d so that the thin web of the connector 220 remains to interconnect the two anchors 182f and 184f.

Although it is preferred to form the anchors 182f and 184f from a single piece of material with a thin web or connector 220 between the two anchors, it is contemplated that the anchors 182f and 184f could be formed from two separate pieces of material and interconnected by a separate connector 220. If this was done, the connector 220 could be formed of a material which is different than the material of the anchors 182f and 184f. For example, the connector 220 could be formed of a suitable polymeric material and bonded to the leading end surface 66f of the anchor 182f and to the trailing end surface 68f of the anchor 184f. If this was done, the polymeric material could be ruptured or broken as the connector 220 is deformed during installation of the anchors 182f and 184f and movement of the anchors to the orientation shown in FIG. 20.

It is also contemplated that the connector 220 could be formed by a plurality of relatively thin elements which are disposed at spaced apart locations along the leading end of the flat outer side surface 30f of the side wall 58f of the anchor 182f and the trailing end of the flat outer side surface 30f of the side wall 58f of the leading anchor 184f. The thin spaced apart connector portions could be integrally formed with the anchors 182f and 184f or could be formed of a suitable connector material which extends between the anchors and used to interconnect them, such as spots or small bodies of adhesive.

Conclusion

In view of the foregoing description, it is apparent that the present invention provides a new and improved method and apparatus for securing a suture 12 in body tissue. An improved suture anchor 10 has a polygonal cross-sectional configuration with an outer side 14 which is formed by a plurality of flat side surface areas 28, 30, and 32 which are interconnected by outer corner portions 22, 24, and 26. The anchor 10 has a passage 18 formed by a plurality of flat inner side surface areas 48, 50, and 52 which are interconnected by a plurality of inner corner portions 40, 42 and 44. The suture 12 is engageable with one of the inner corner portions 40, 42 or 44 to urge an outer corner portion 22, 24, or 26 of the anchor 10 into engagement with body tissue 72. A groove 162 may be provided in the end and/or outer side of the anchor to receive the suture.

A plurality of anchors 182 and 184 having the configuration of the anchor 10 or a different configuration may be used to anchor a suture. When a plurality of anchors are used, the suture 12 is inserted through each of the anchors and the anchors are sequentially moved into the body tissue. As a leading anchor 184 is moved into the body tissue, the suture 12 is tensioned to move a corner portion 22 on the leading anchor into engagement with the body tissue. A connector 220 may be provided between each anchor.

What is claimed is:

1. A method of anchoring a suture in bone, said method comprising the steps of moving a suture anchor through an opening in a compact outer layer of bone into cancellous bone which is enclosed by the compact outer layer of bone, said step of moving a suture anchor through an opening in a compact outer layer of bone is performed with a suture connected with the suture anchor, thereafter, tensioning the suture, and retaining the suture anchor against movement relative to and in a spaced apart relationship with the compact outer layer of bone against the influence of force transmitted from the suture to the suture anchor during tensioning of the suture, said step of retaining the suture anchor against movement relative to the compact outer layer of bone includes transmitting force between the suture anchor and the cancellous bone while the suture anchor is spaced from the compact outer layer of bone.

2. A method as set forth in claim 1 further including the step of changing the orientation of the suture anchor relative to the compact outer layer of bone after performing said step of moving the suture anchor through the opening in the compact outer layer of bone.

3. A method as set forth in claim 1 wherein said step of tensioning the suture includes pulling on first and second portions of the suture which extend from the suture anchor through the opening in the compact outer layer of bone.

4. A method as set forth in claim 1 wherein said step of transmitting force between the suture anchor and the cancellous bone includes pressing an outer surface area on the suture anchor against cancellous bone disposed between the compact outer layer of bone and the outer surface area on the suture.

5. A method as set forth in claim 1 further including the steps of moving the suture anchor relative to the compact outer layer of bone, and moving cancellous bone relative to the compact outer layer of bone under the influence of force transmitted from the suture anchor to the cancellous bone during movement of the suture anchor relative to the compact outer layer of bone.

6. A method as set forth in claim 1 wherein the suture anchor has a corner portion, said method further including the step of pressing the corner portion of the suture anchor against the cancellous bone under the influence of force transmitted from the suture to the suture anchor during tensioning of the suture.

7. A method as set forth in claim 1 further including the step of rotating the suture anchor about the corner portion of the suture anchor while performing said steps of pressing the corner portion of the suture anchor against the cancellous bone and tensioning the suture.

8. A method as set forth in claim 1 wherein said step of moving a suture anchor through an opening in a compact outer layer of bone includes moving the suture anchor through the opening with a first end portion of the suture anchor leading and a second end portion of the suture anchor trailing, after moving the suture anchor through the opening in a compact outer layer of bone, moving the first end portion of the suture anchor to a location offset in a first direction from a central axis of the opening in the compact outer layer of bone and moving the second end portion of the suture anchor to a location offset in a second direction from a central axis of the opening in the compact outer layer of bone, the first and second end portions of the suture anchor being separated from the compact outer layer of bone by cancellous bone when the first end portion of the suture anchor is disposed at the location offset in a first direction from the central axis of the opening in the compact outer layer of bone and the second end portion of the suture anchor is disposed at the location offset in a second direction from the central axis of the opening in the compact outer layer of bone, said step of retaining the suture anchor against movement relative to the compact outer layer of bone includes maintaining the first end portion of the suture anchor stationary in and completely surrounded by cancellous bone offset in the first direction from the central axis of the opening in the compact outer layer of bone and maintaining the second end portion of the suture anchor stationary in and completely surrounded by cancellous bone offset in the second direction from the central axis of the opening in the compact outer layer of bone.

9. A method as set forth in claim 1 wherein said step of moving a suture anchor through an opening in a compact outer layer of bone includes moving the suture anchor through the opening with a first end portion of the suture anchor leading and a second end portion of the suture anchor trailing, said method further includes moving the second end portion of the suture anchor into cancellous bone adjacent to one side of the opening, rotating the suture anchor about the second end portion of the suture anchor, and moving the first end portion of the suture anchor through cancellous bone adjacent to a second side of the opening, said steps of rotating the suture anchor about the second end portion of the suture anchor and moving the first end portion of the suture anchor through cancellous bone being performed with said first and second end portions of the suture anchor spaced apart from the compact outer layer of bone.

10. A method as set forth in claim 1 wherein said step of moving a suture anchor through an opening in a compact outer layer of bone includes moving the suture anchor through the opening with a first end portion of the suture anchor leading and a second end portion of the suture anchor trailing, said method further includes moving the first end portion of the suture anchor back toward the opening by rotating the suture anchor about the second end portion of the suture anchor, and embedding the first and second end portions of the suture anchor in the cancellous bone with a central axis of the opening in the compact outer layer of bone extending through the suture anchor.

11. A method as set forth in claim 1 wherein said step of moving a suture anchor through an opening in a compact outer layer of bone into cancellous bone includes moving the suture anchor into the cancellous bone for a distance which is greater than a distance between a leading end and a trailing end of the suture anchor, and changing the orientation of the suture anchor relative to the compact outer layer of bone while maintaining the leading and trailing ends of the suture anchor spaced from the compact outer layer of bone, said step of changing the orientation of the suture anchor includes moving the suture anchor to a position in which the suture anchor extends across the opening in the compact outer layer of bone with the leading and trailing ends of the suture anchor spaced from the compact outer layer of bone.

12. A method of anchoring a suture in bone, said method comprising the steps of moving the suture anchor through a compact outer layer of bone into cancellous bone, and embedding the suture anchor in a matrix of the cancellous bone with opposite end portions of the suture anchor completely enclosed by the cancellous bone.

13. A method as set forth in claim 12 further including the steps of tensioning a suture connected with the suture anchor and transmitting forces resulting from tensioning of the suture to only cancellous bone from outer surfaces of the suture anchor.

14. A method as set forth in claim 12 wherein said step of embedding the suture anchor in matrix of the cancellous bone includes moving the suture anchor to a position in which a portion of the suture anchor disposed between the first and second end portions of the suture anchor spans an opening in the compact outer layer of bone.

15. A method as set forth in claim 12 wherein said step of moving the suture anchor through a compact outer layer of bone into cancellous bone is performed with the suture anchor disposed in engagement with an inserter member, said step of embedding the suture anchor in cancellous bone includes moving the suture anchor relative to the inserter member while maintaining a portion of the inserter member in engagement with the suture anchor, said step of moving the suture anchor relative to the inserter member includes changing the orientation of the suture anchor relative to the compact outer layer of bone.

16. A method as set forth in claim 12 wherein said step of embedding the suture anchor in a matrix of cancellous bone includes pushing aside cancellous bone with the first end portion of the suture anchor and pushing aside cancellous bone with the second end portion of the suture anchor to move the first and second end portions of the suture anchor into the cancellous bone to locations where the first and second end portions of the suture anchor are completely enclosed by the cancellous bone.

17. A method as set forth in claim 12 wherein said step of moving the suture anchor through a compact outer layer of bone includes moving the suture anchor with the first end portion of the suture anchor leading and a second end portion of the suture anchor trailing, said step of embedding the suture anchor in a matrix of cancellous bone includes the steps of engaging the cancellous bone with the second end portion of the suture anchor and rotating the suture anchor about the second end portion of the suture anchor.

18. A method as set forth in claim 12 wherein said step of moving the suture anchor through a compact outer layer of bone includes moving the suture anchor through the compact outer layer of bone with the first end portion of the suture anchor leading and a second end portion of the suture anchor trailing, said step of embedding the suture anchor in a matrix of cancellous bone includes rotating the suture anchor to move the first end portion of the suture anchor from a location spaced a first distance from the compact outer layer of bone to a location spaced a second distance from the compact outer layer of bone, the second distance being smaller than the first distance.

19. A method as set forth in claim 12 wherein one of the end portions of the suture anchor includes a flat side surface area, said step of embedding the suture anchor in a matrix of cancellous bone includes transmitting force from the flat side surface area on the one end portion of the suture anchor to the cancellous bone and moving cancellous bone relative to the compact outer layer of bone under the influence of force transmitted from the flat side surface area on the one end portion of the suture anchor.

20. A method as set forth in claim 12 further including the step of forming an opening which extends through the compact outer layer of bone into the cancellous bone, the opening having an extent in the cancellous bone which is greater than a distance between opposite ends of the suture anchor, said step of moving the suture anchor through the compact outer layer of bone into cancellous bone includes moving the suture anchor into the opening through a distance which is sufficient to move the opposites ends of the suture anchor into the portion of the opening disposed in the cancellous bone, said step of embedding the suture anchor in the cancellous bone includes moving one end of the suture anchor into cancellous bone disposed along one side of the opening and moving an end of the suture anchor opposite from the one end into cancellous bone disposed along a side of the opening opposite from the one side.

21. A method of anchoring a suture in bone, said method comprising the steps of connecting a suture with the suture anchor with first and second portions of the suture extending away from the suture anchor and a connector portion of the suture extending between the first and second portions of the suture and through an opening in the suture anchor, forming an opening which extends through a compact outer layer of the bone into cancellous bone which is enclosed by the compact outer layer of bone, said step of forming an opening includes forming the opening with a depth in the cancellous bone which is greater than a distance between first and second end portions of the suture anchor, pressing the suture anchor against an end portion of an inserter member under the influence of force transmitted through the first and second portions of the suture, moving the suture anchor and the end portion of the inserter member through a portion of the opening disposed in the compact outer layer of bone into a portion of the opening disposed in the cancellous bone while engaging the suture anchor with the end portion of the inserter member, said step of moving the suture anchor through the portion of the opening disposed in the compact outer layer of bone into the portion of the opening disposed in the cancellous bone is performed with the first end portion of the suture anchor leading and the second end portion of the suture anchor trailing, thereafter, changing the orientation of the suture anchor relative to the compact outer layer of bone, withdrawing the end portion of the inserter member from the opening which extends through the compact outer layer of bone into the cancellous bone, and retaining the suture anchor against movement relative to the compact outer layer of bone under the influence of force transmitted to the suture anchor through the first and second portions of the suture by pressing surfaces on the suture anchor against only the cancellous bone while the suture anchor is maintained in a spaced apart relationship with the compact outer layer of bone.

22. A method as set forth in claim 21 wherein said step of changing the orientation of the suture anchor relative to the compact outer layer of bone includes moving the second end portion of the suture anchor into the cancellous bone in a direction transverse to a central axis of the opening which extends through the compact outer layer of bone into the cancellous bone, said step of moving the second end portion of the suture anchor into the cancellous bone in a direction transverse to the central axis of the opening which extends through the compact outer layer of bone includes maintaining the second end portion of the suture anchor in a spaced apart relationship with the compact outer layer of bone, moving the first end portion of the suture anchor into the cancellous bone in a direction transverse to the central axis of the opening which extends through the compact outer layer of bone into the cancellous bone, said step of moving the first end portion of the suture anchor into the cancellous bone in a direction transverse to the central axis of the opening which extends through the compact outer layer of bone into the cancellous bone includes maintaining the first end portion of the suture anchor in a spaced apart relationship with the compact outer layer of bone, at least one of said steps of moving the first end portion and moving the second end portion of the suture anchor into the cancellous bone is at least partially performed while engaging the end portion of the inserter member with the suture anchor and while the end portion of the inserter member is disposed in a portion of the opening disposed in the cancellous bone, at least one of said steps of moving the first end portion and moving the second end portion of the suture anchor into the cancellous bone is at least partially performed while tensioning at least one of the first and second portions of the suture to transmit force to the suture anchor.

23. A method as set forth in claim 21 wherein said step of changing the orientation of the suture anchor includes engaging cancellous bone disposed along a first side portion of the opening which extends through the compact outer layer of bone into the cancellous bone with the second end portion of the suture anchor, rotating the suture anchor about an axis which extends through the cancellous bone, engaging cancellous bone disposed along a second side portion of the opening which extends through the compact outer layer of bone into the cancellous bone with the first end portion of the suture anchor, said step of rotating the suture anchor is at least partially performed while engaging the suture anchor with the end portion of the inserter member and includes transmitting force to the suture anchor through at least one of the first and second portions of the suture.

24. A method as set forth in claim 21 wherein said step of changing the orientation of the suture anchor relative to the compact outer layer of bone includes embedding the first end portion of the suture anchor in the cancellous bone at a location spaced from the compact outer layer of bone and embedding the second end portion of the suture anchor in the cancellous bone at a location spaced from the compact outer layer of bone.

25. A method as set forth in claim 21 wherein said step of changing the orientation of the suture anchor relative to the compact outer layer of bone includes moving the first end portion of the suture anchor along a path which extends through the cancellous bone toward the compact outer layer of bone by transmitting force to the suture anchor through the suture and rotating the suture anchor about an axis which extends through the cancellous bone at a location adjacent to the suture anchor.

26. A method as set forth in claim 21 wherein said step of moving the suture anchor through a portion of the opening disposed in the compact outer layer of bone into a portion of the opening disposed in the cancellous bone is performed with a flat surface on the suture anchor extending parallel to a central axis of the opening, said step of changing the orientation of the suture anchor relative to the compact outer layer of bone includes pressing the flat surface on the suture anchor against the cancellous bone and moving cancellous bone under the influence of force applied against the cancellous bone by the flat surface on the suture anchor.

27. A method as set forth in claim 21 wherein said step of moving the suture anchor through a portion of the opening disposed in the compact outer layer of bone into a portion of the opening disposed in the cancellous bone includes moving a flat side surface area on the first end portion of the suture anchor along a central axis of opening with the flat side surface area extending along a path of movement of the suture anchor, said step of changing the orientation of suture anchor relative to the compact outer layer of bone includes rotating the suture anchor about an axis which is disposed adjacent to the second end portion of the anchor and moving the flat side surface along an arcuate path which extends through the cancellous bone in a direction toward the compact outer layer of bone and transverse to the flat side surface area on the suture anchor.

28. A method of anchoring a suture in bone, said method comprising the steps of moving the suture anchor along a first path through a compact outer layer of bone into cancellous bone with a flat surface area on a first end portion of the suture anchor extending along the first path, and positioning the suture anchor in the cancellous bone with first and second end portions of the suture anchor spaced from the compact outer layer of bone, said step of positioning the suture anchor in the cancellous bone includes rotating the suture anchor about an axis disposed adjacent to the second end portion of the suture anchor to move the first end portion of the suture anchor toward the compact outer layer of bone along an arcuate path which extends transverse to the flat surface area on the first end portion of the suture anchor, applying force against cancellous bone with the flat surface area on the first end portion of the suture anchor while performing said step of rotating the suture anchor, moving cancellous bone under the influence of fore applied against the cancellous bone by the flat surface area on the first end portion of the suture anchor while rotating the suture anchor, and interrupting said step of rotating the suture anchor with the first and second end portions of the suture anchor spaced from the compact outer layer of bone and with the flat surface area on the first end portion of the suture anchor extending transverse to the first path.

29. A method as set forth in claim 28 wherein said step of interrupting rotation of the suture anchor is performed with the first path extending through a portion of the suture anchor disposed between the first and second end portions of the suture anchor.

30. A method as set forth in claim 28 wherein said step of moving the suture anchor along the first path is at least partially performed with the flat surface area on the first end portion extending parallel to a longitudinal central axis of the first path.

31. A method as set forth in claim 28 wherein said step of moving the suture anchor along a first path includes moving the suture anchor with the first end portion of the suture anchor leading and the second end portion of the suture anchor trailing.

32. A method of anchoring a suture in bone, said method comprising the steps of connecting a suture with the suture anchor, forming an opening which extends through a compact outer layer of bone into cancellous bone which is enclosed by the compact outer layer of bone, moving the suture anchor along a first path through a portion of the opening disposed in the compact outer layer of bone into a portion of the opening disposed in the cancellous bone with a first end portion of the suture anchor leading and a second end portion of the suture anchor trailing, and moving the suture anchor to a position in which the first and second end portions of the suture anchor are spaced from the compact outer layer of bone and a portion of the suture anchor disposed between the first and second end portions extends across the first path and is spaced from the compact outer layer of bone.

33. A method as set forth in claim 32 wherein said step of moving the suture anchor to the position in which the first and second end portions of the suture anchor are spaced from the compact outer layer of bone and the portion of the suture anchor disposed between the first and second end portions extends across the first path includes moving the second end portion of the suture anchor into cancellous bone along a first side of the first path, tensioning the suture, and after moving the second end portion of the suture anchor into cancellous bone, rotating the suture anchor to move the first end portion of the suture anchor through cancellous bone along a second side of the first path in a direction toward the compact outer layer of bone, said step of rotating the suture anchor includes rotating the suture anchor about a location where the second end portion of the suture anchor engages the cancellous bone.

34. A method as set forth in claim 32 wherein said step of moving the suture anchor to a position in which the first and second end portions of the suture anchor are spaced from the compact outer layer of bone and a portion of the suture anchor disposed between the first and second end portions extends across the first path includes moving a corner where surfaces on the first end portion of the suture anchor converge into cancellous bone disposed along a first side of the first path, and moving a corner where surfaces on the second end portion of the anchor converge into cancellous bone along a second side of the first path.

35. A method as set forth in claim 32 wherein said step of moving the suture anchor to a position in which the first and second end portions of the suture anchor are spaced from the compact outer layer of bone and a portion of the suture anchor disposed between the first and second end portions extends across the first path includes pressing a flat surface area on the first end portion of the suture anchor against cancellous bone disposed along a first side of the first path, moving a portion of the cancellous bone disposed along the first side of the first path under the influence of force applied against the cancellous bone disposed along the first side of the first path by the flat surface area on the first end portion of the suture anchor, pressing a flat surface area on the second end portion of the suture anchor against cancellous bone disposed along a second side of the first path, and moving a portion of the cancellous bone disposed along the second side of the first path under the influence of force applied against the cancellous bone disposed along the second side of the first path by the flat surface area on the second end portion of the suture anchor.

36. A method as set forth in claim 32 wherein said step of moving the suture anchor to a position in which the first and second end portions of the suture anchor are spaced from the compact outer layer of bone and a portion of the suture anchor disposed between the first and second end portions extends across the first path includes embedding the first end portion of the suture anchor in cancellous bone along a first side of the first path with the first end portion of suture anchor completely enclosed by cancellous bone and embedding the second end portion of the suture anchor in cancellous bone along a second side of the first path with the second end portion of the suture anchor completely enclosed by cancellous bone.

37. A method of anchoring a suture in bone, said method comprising the steps of connecting a suture with the suture anchor, forming an opening which extends through a compact outer layer of bone into cancellous bone which is enclosed by the compact outer layer of bone, engaging the suture anchor with an inserter member, moving the suture anchor and an end portion of the inserter member into the opening formed in the bone with a first end portion of the suture anchor leading and a second end portion of the suture anchor trailing, said step of moving the suture anchor and an end portion of the inserter member into the opening includes moving the suture anchor through the compact outer layer of bone into a portion of the opening formed in the cancellous bone to a position in which the second end portion of the suture anchor is disposed adjacent to cancellous bone and is spaced from the compact outer layer of bone, rotating the suture anchor about an axis of rotation which extends transverse to and is offset in a first direction from a longitudinal central axis of the inserter member, said step of rotating the suture anchor includes moving the first end portion of the suture anchor into cancellous bone which is offset in a second direction from the longitudinal central axis of the inserter member, moving the second end portion of the suture anchor into cancellous bone which is offset in the first direction from the longitudinal central axis of the inserter member, tensioning the suture to transmit force to the suture anchor to promote rotation of the suture anchor, disengaging the inserter member from the suture anchor, moving the suture anchor to a position in which the first and second end portions of the suture anchor are embedded in the cancellous bone and are spaced from the compact outer layer of bone, and retaining the suture anchor against movement relative to the compact outer layer of bone against the influence of force transmitted through the suture to the suture anchor under the influence of only forces applied against the suture anchor by the cancellous bone.

38. A method as set forth in claim 37 wherein said step of rotating the suture anchor about an axis of rotation which extends transverse to and is offset in a first direction from a longitudinal central axis of the inserter member includes initiating rotation of the suture anchor about the axis of rotation with the axis of rotation offset a first distance in the first direction from the longitudinal central axis of the inserter member and interrupting rotation of the suture anchor about the axis of rotation with the axis of rotation offset a second distance in the first direction from the longitudinal central axis of the inserter member, the second distance being greater than the first distance.

39. A method as set forth in claim 37 wherein said step of rotating the suture anchor about an axis of rotation which extends transverse to and is offset in a first direction from a longitudinal central axis of the inserter member is at least partially performed while the inserter member is disposed in engagement with the suture anchor.

40. A method as set forth in claim 37 wherein said step of tensioning the suture to transmit force to the suture anchor is at least partially performed while the inserter member is disposed in engagement with the suture anchor to promote rotation of the suture anchor relative to the inserter member.

41. A method as set forth in claim 37 wherein said step of moving the second end portion of the suture anchor into cancellous bone which is offset in the first direction from the longitudinal central axis of the inserter member is performed after at least partially performing said step of rotating the suture anchor.

42. A method as set forth in claim 37 wherein the first end portion of the suture anchor includes a flat surface area, said step of moving the suture anchor and an end portion of the inserter member into the opening formed in the bone is performed with the flat surface area on the first end portion of the suture anchor extending along the longitudinal central axis of the inserter member, said step of rotating the suture anchor about an axis of rotation includes pressing the flat surface area on the first end portion of the suture anchor against cancellous bone and moving cancellous bone under the influence of force applied against the cancellous bone by the flat surface area on the first end portion of the suture anchor.

* * * * *